（12） United States Patent
Yamaya

(10) Patent No.: US 11,096,558 B2
(45) Date of Patent: Aug. 24, 2021

(54) ENDOSCOPE COVER, ENDOSCOPE, AND COVER UNIT

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 441 days.

(21) Appl. No.: 16/034,958

(22) Filed: Jul. 13, 2018

(65) Prior Publication Data

US 2018/0317742 A1    Nov. 8, 2018

Related U.S. Application Data

(63) Continuation of application No. PCT/JP2017/000674, filed on Jan. 11, 2017.

(30) Foreign Application Priority Data

Jan. 14, 2016  (JP) .............................. JP2016-005543

(51) Int. Cl.
*A61B 1/00*        (2006.01)
*A61B 1/05*        (2006.01)
(Continued)

(52) U.S. Cl.
CPC ........ *A61B 1/0008* (2013.01); *A61B 1/00098* (2013.01); *A61B 1/00137* (2013.01);
(Continued)

(58) Field of Classification Search
CPC . A61B 1/0008; A61B 1/00138; A61B 1/0676; A61B 1/00098; A61B 1/00101; A61B 1/00089; G02B 23/2476
See application file for complete search history.

(56) References Cited

U.S. PATENT DOCUMENTS 4,555,100 A * 11/1985 Ditto .................. B25B 5/166
269/166
2008/0021274 A1* 1/2008 Bayer ................ A61B 1/0676
600/112
(Continued)

FOREIGN PATENT DOCUMENTS

JP    H09299315 A    11/1997
JP    H10127578 A    5/1998
(Continued)

OTHER PUBLICATIONS

English translation of International Preliminary Report on Patentability dated Jul. 26, 2018 together with the Written Opinion received in related International Application No. PCT/JP2017/000674.

(Continued)

*Primary Examiner* — Aaron B Fairchild
(74) *Attorney, Agent, or Firm* — Scully, Scott, Murphy & Presser, P.C.

(57) ABSTRACT

An endoscope cover includes: a cylindrical cover main body that is to be attached to a distal framing portion along a longitudinal axis of an insertion section, and that includes an annular portion which is to cover part of an outer periphery of the distal framing portion; and a fragile portion, at least part of which is provided on the annular portion of the cover main body. The cover main body is spaced apart from at least part of the distal framing portion, and forms a gap between the cover main body and the distal framing portion. The fragile portion is broken under application of an intended stress and configured to have a user recognize breakage of the fragile portion in cooperation with the gap.

15 Claims, 30 Drawing Sheets

(51) Int. Cl.
*A61B 1/06* (2006.01)
*G02B 23/26* (2006.01)
*G02B 23/24* (2006.01)

(52) U.S. Cl.
CPC .............. *A61B 1/05* (2013.01); *A61B 1/0676* (2013.01); *G02B 23/24* (2013.01); *G02B 23/26* (2013.01); *G02B 23/2476* (2013.01)

(56) References Cited

U.S. PATENT DOCUMENTS

| | | | |
|---|---|---|---|
| 2008/0103357 A1* | 5/2008 | Zeiner .................. | A61B 1/0014 600/104 |
| 2017/0000317 A1* | 1/2017 | Iizuka ...................... | A61B 1/00 |
| 2017/0238789 A1* | 8/2017 | Iizuka ................ | A61B 1/00089 |
| 2018/0228348 A1* | 8/2018 | Yamaya ................. | G02B 23/24 |
| 2018/0289245 A1* | 10/2018 | Yamaya ............. | A61B 1/00098 |
| 2018/0317741 A1* | 11/2018 | Yamaya ................ | A61B 1/0008 |
| 2019/0015172 A1* | 1/2019 | Yamaya ............. | A61B 1/00101 |
| 2019/0142242 A1* | 5/2019 | Yamaya ................. | G02B 23/24 600/101 |
| 2019/0208992 A1* | 7/2019 | Yamaya ............. | A61B 1/00089 |
| 2020/0037860 A1* | 2/2020 | Yamaya ................. | G02B 23/24 |

FOREIGN PATENT DOCUMENTS

| | | |
|---|---|---|
| JP | 2003102668 A | 4/2003 |
| JP | 2007289434 A | 11/2007 |

OTHER PUBLICATIONS

International Search Report dated Mar. 21, 2017 issued in PCT/JP2017/000674.

* cited by examiner

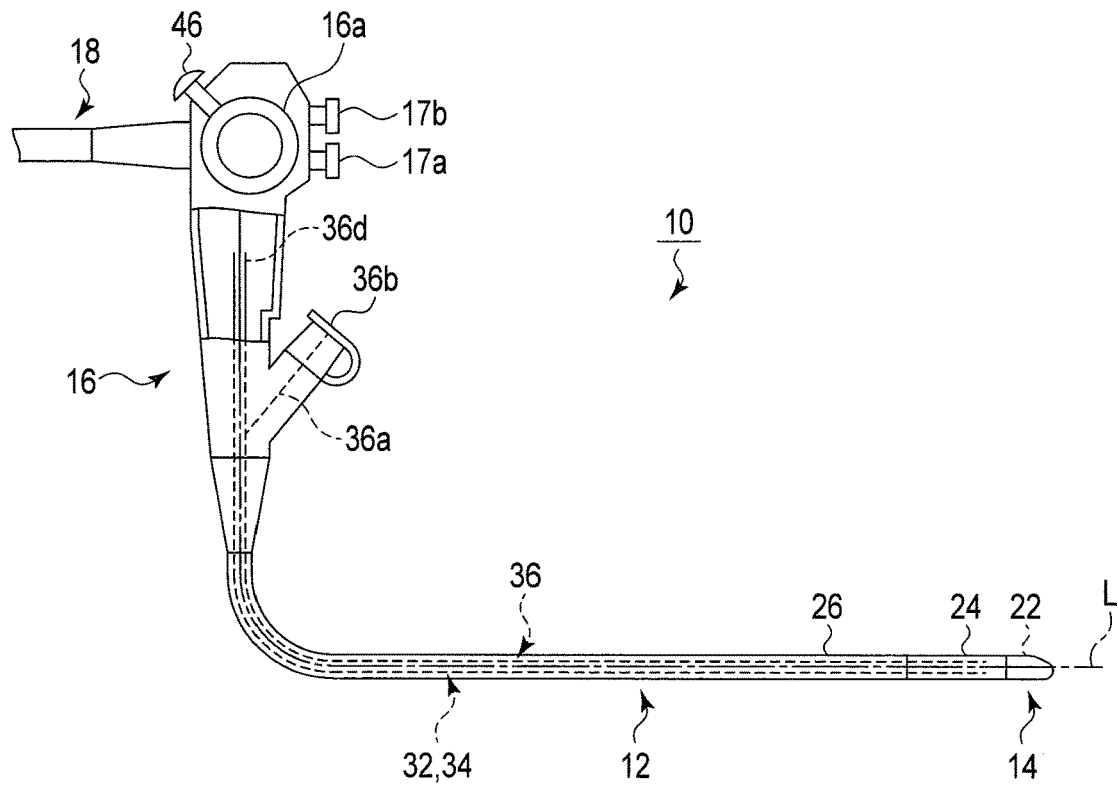
F I G. 1
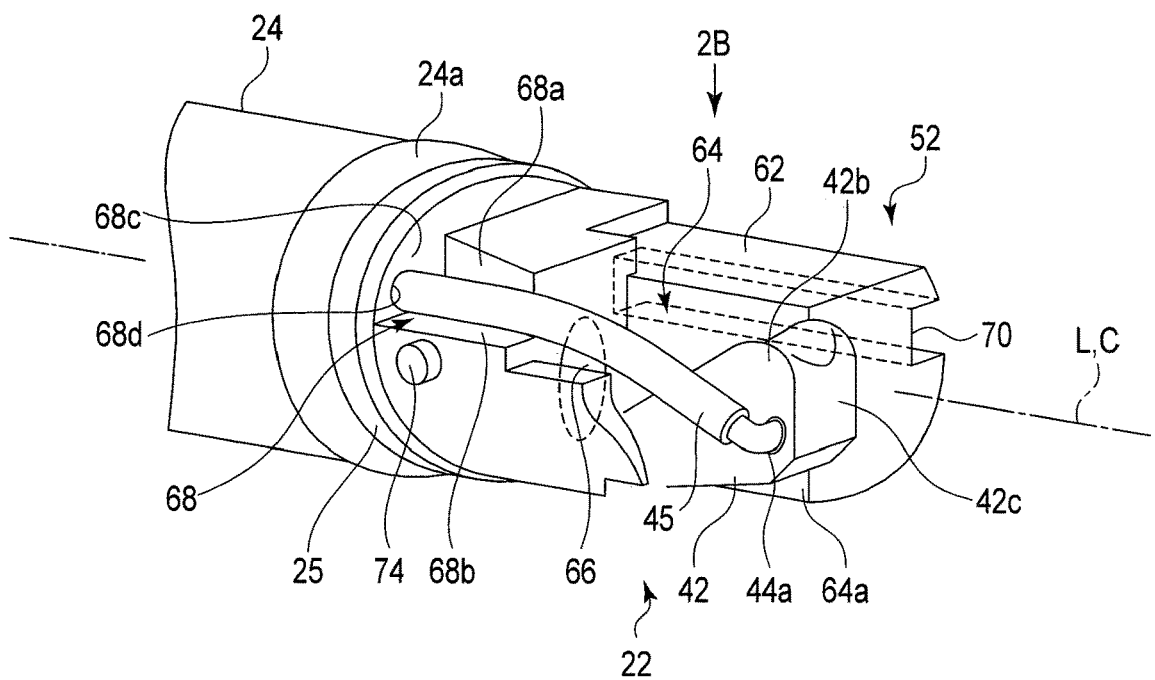
F I G. 2A

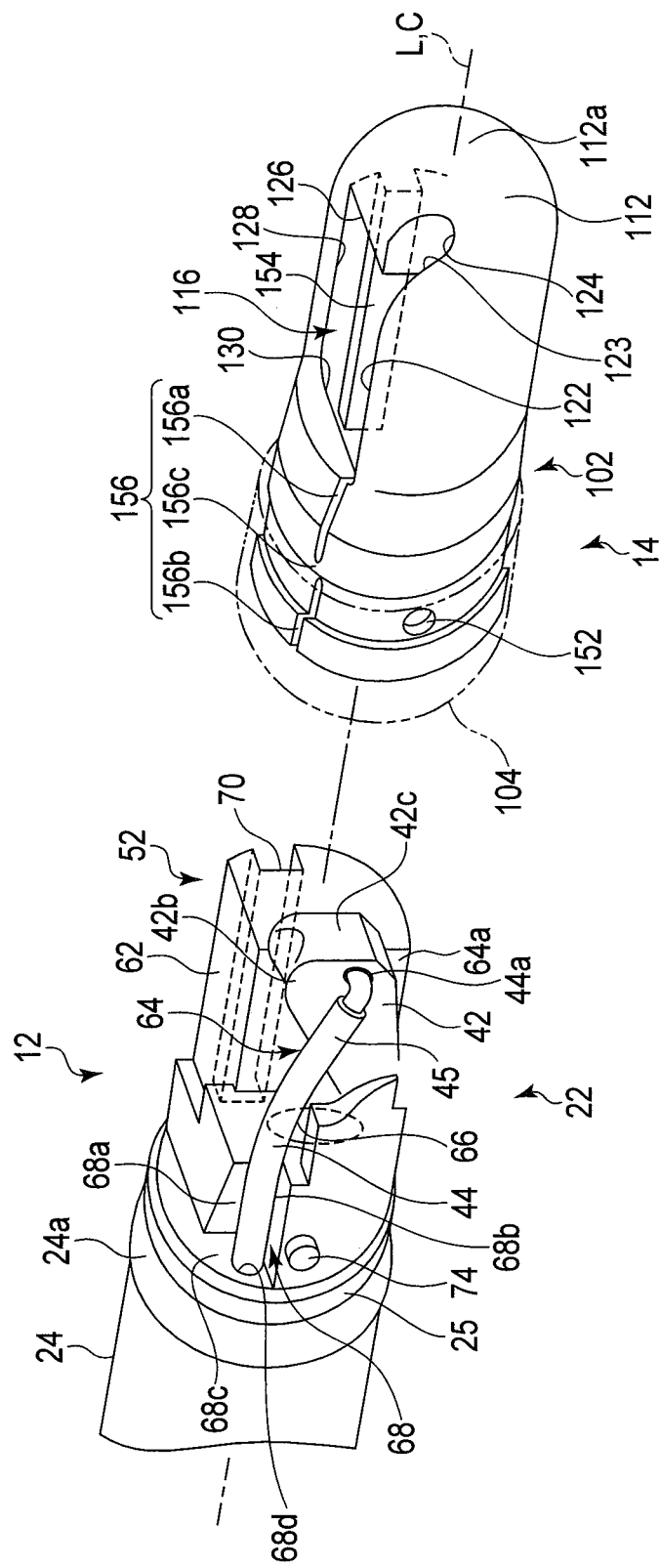
F I G. 6

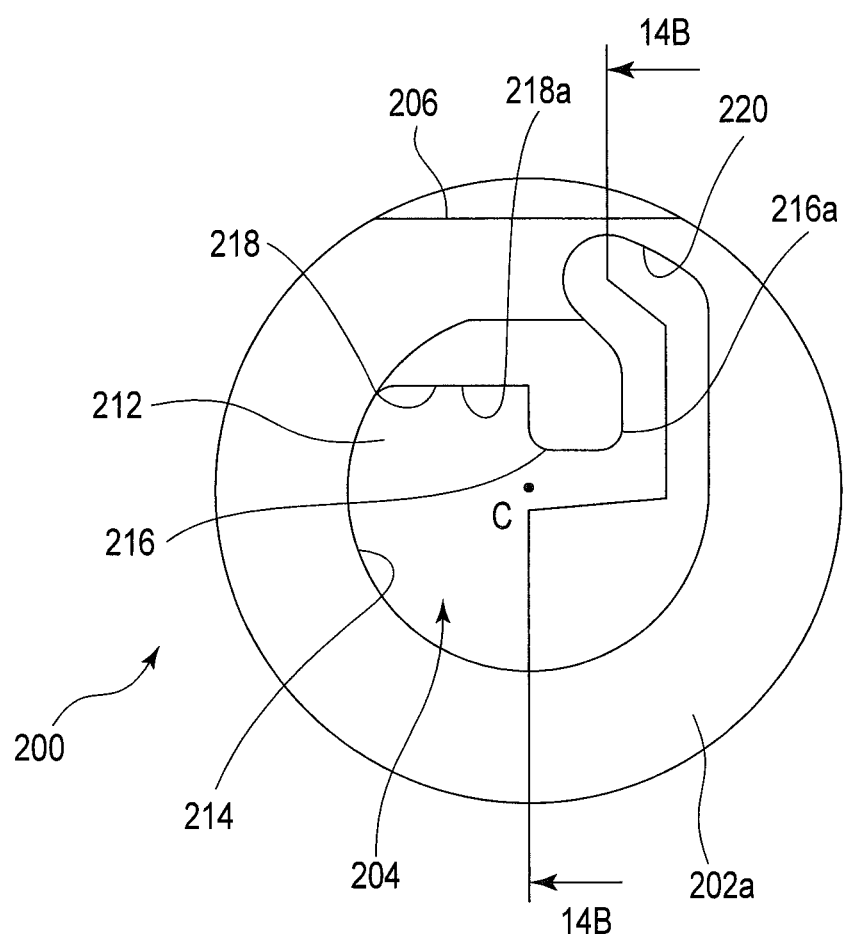
F I G. 14A

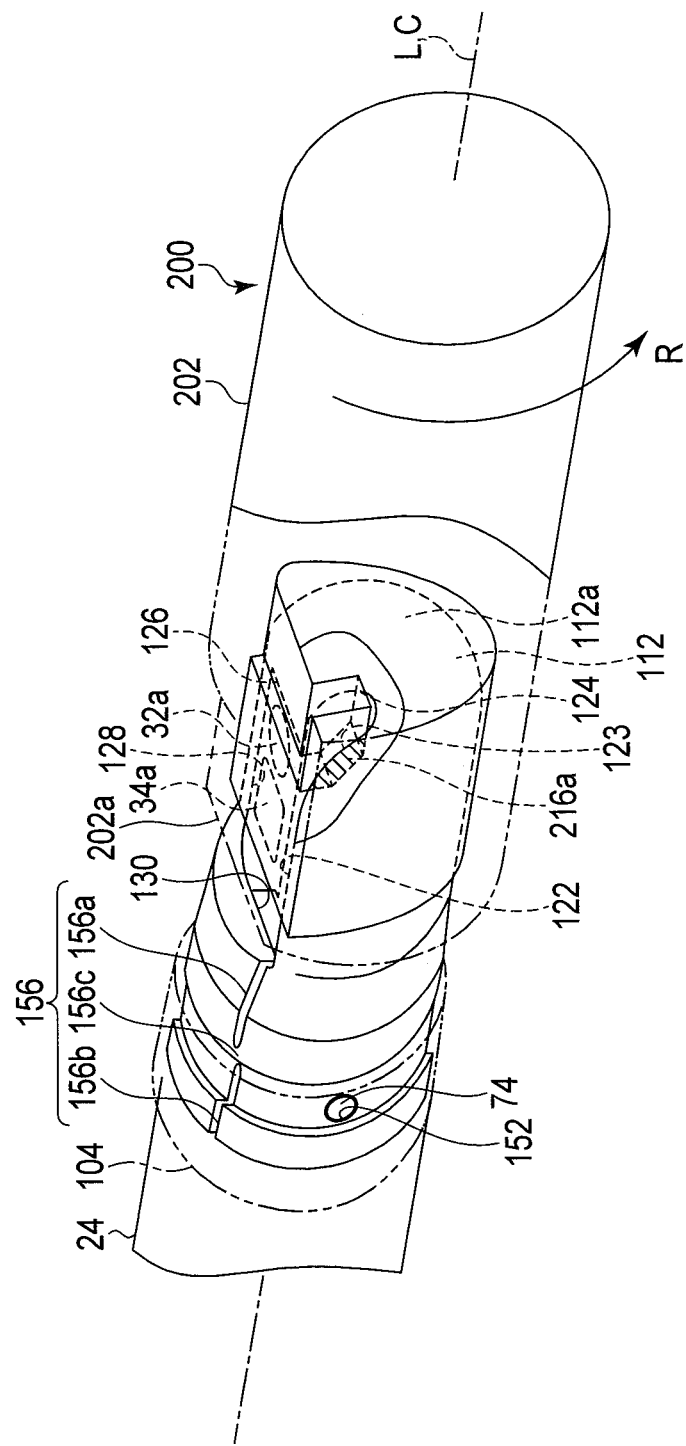
F I G. 15B

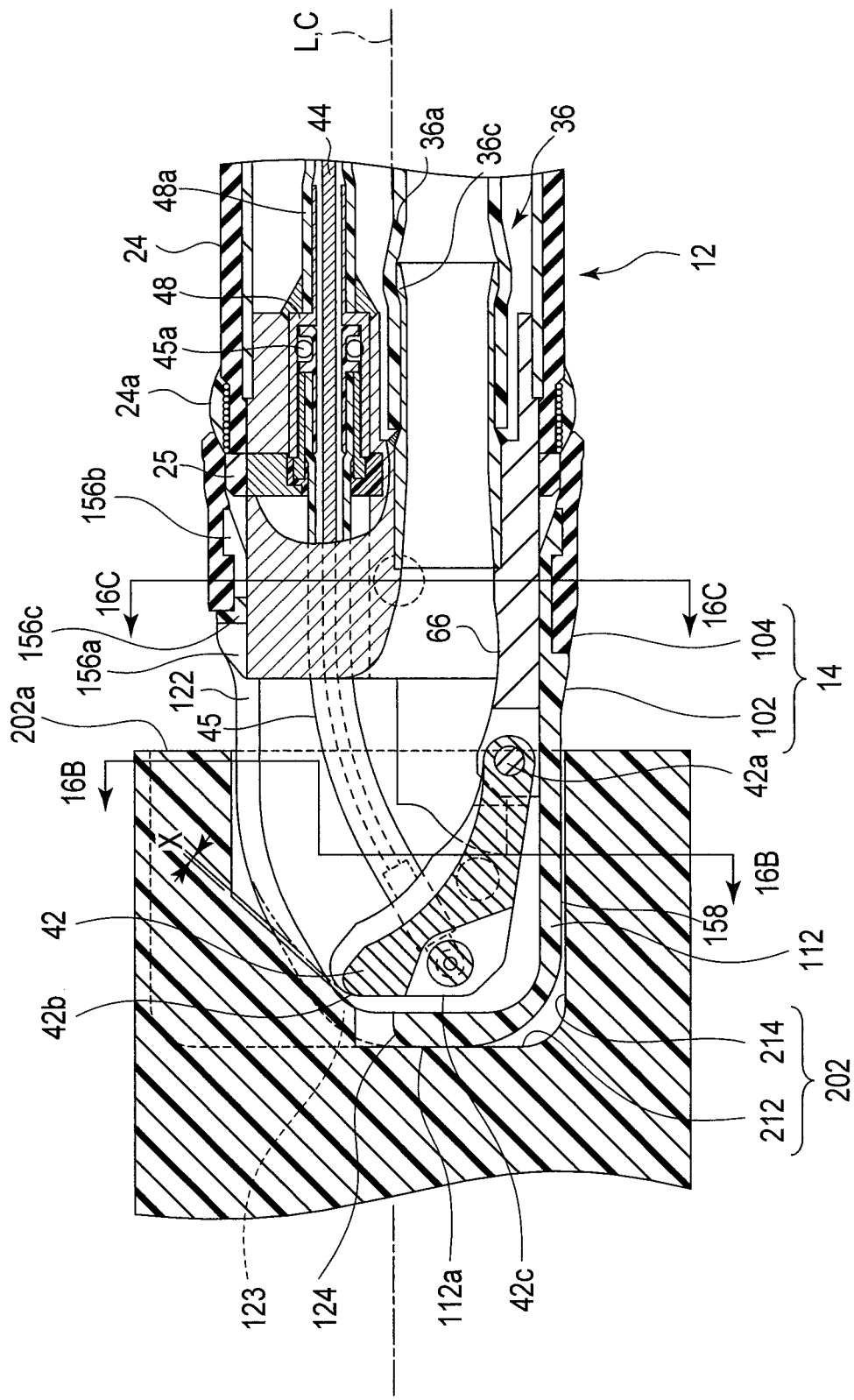
F I G. 16A

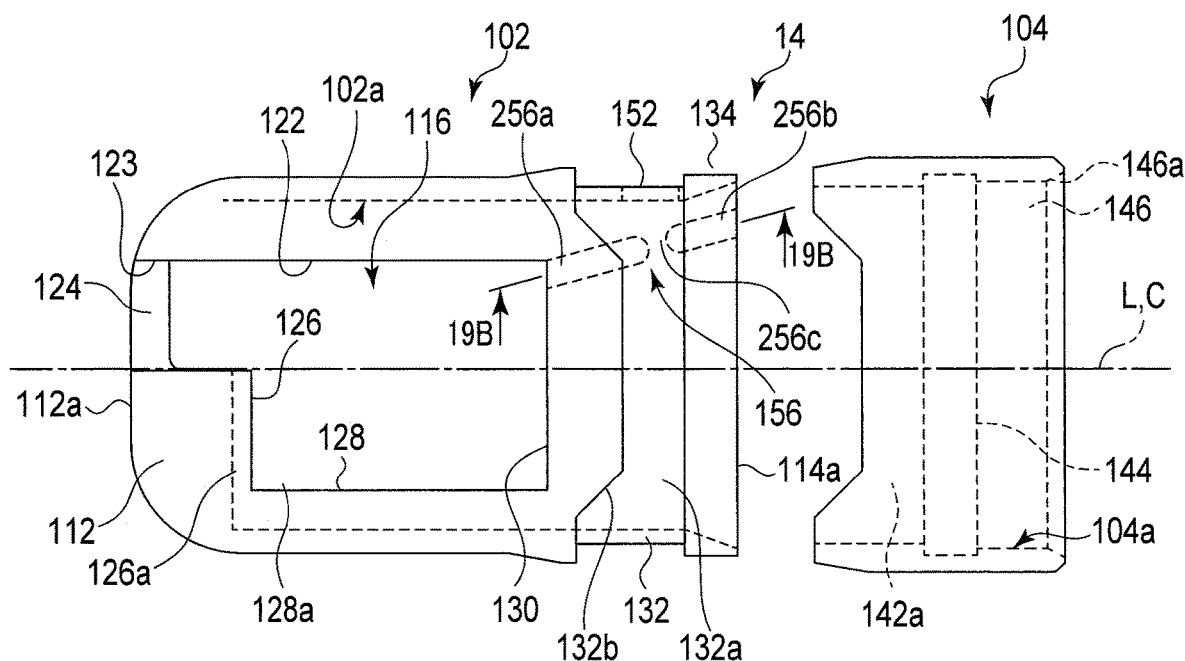
F I G. 19A
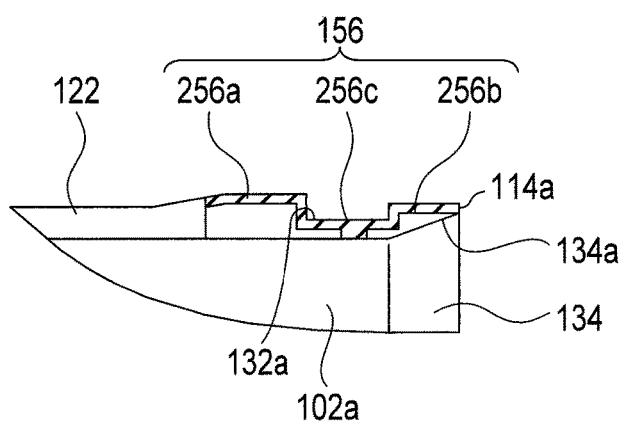
F I G. 19B

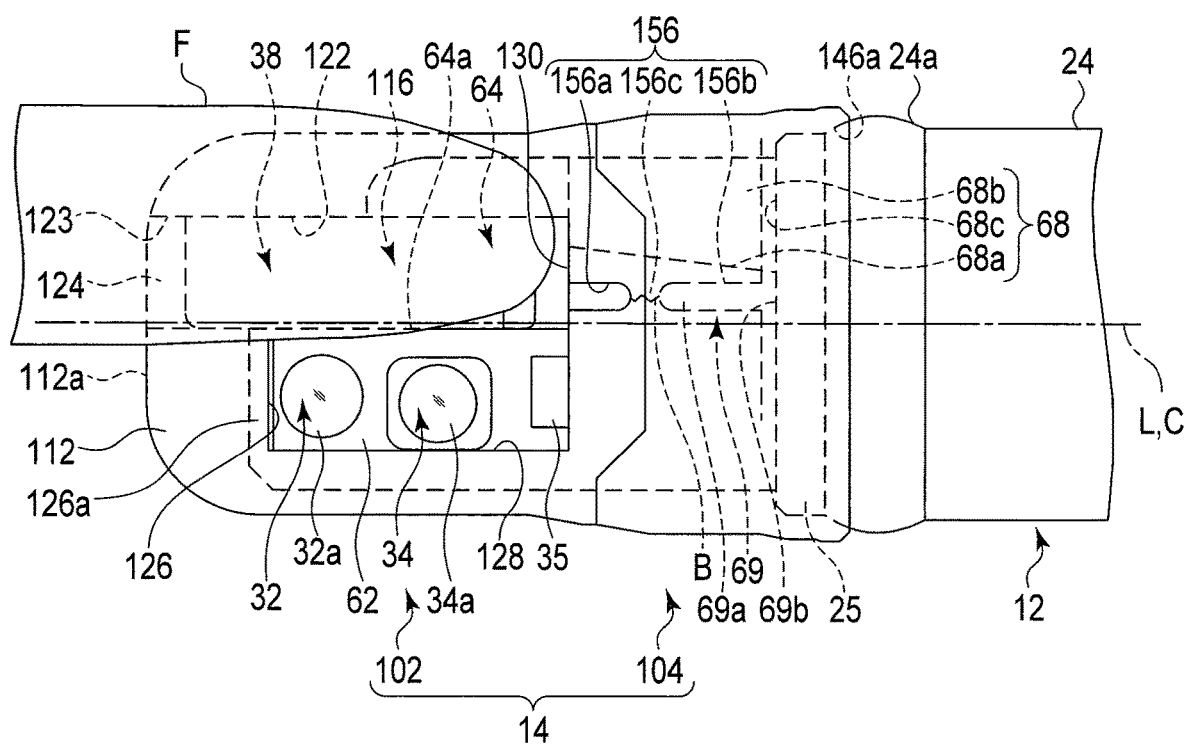
F I G. 27

ENDOSCOPE COVER, ENDOSCOPE, AND COVER UNIT

CROSS-REFERENCE TO RELATED APPLICATIONS

This application is a Continuation Application of PCT Application No. PCT/JP2017/000674, filed Jan. 11, 2017 and based upon and claiming the benefit of priority from prior Japanese Patent Application No. 2016-005543, filed Jan. 14, 2016, the entire contents of all of which are incorporated herein by reference.

1. FIELD OF THE INVENTION

This invention relates to an endoscope cover that is to be attached to a distal framing portion of an insertion section of an endoscope, an endoscope that includes such an endoscope cover, and a cover unit.

2. DESCRIPTION OF THE RELATED ART

Jpn. Pat. Appln. KOKAI Publication No. 2003-102668, for example, discloses a cover that is to be attached to a distal framing portion of an insertion section of an endoscope. The cover is removed by tearing along a groove formed from an edge at its proximal end to its distal end. For the removal of the cover from the distal framing portion, the tearing of the cover from the proximal edge toward the distal side may be performed using a tool or fingers.

BRIEF SUMMARY OF THE INVENTION

According to one aspect of the present invention, an endoscope cover that is to be attached to a distal framing portion of an insertion section of an endoscope, includes: a cylindrical cover main body that is to be attached to the distal framing portion along a longitudinal axis of the insertion section, the cover main body including an annular portion that is to cover a part of an outer periphery of the distal framing portion, and the cover main body being spaced apart from at least a part of the distal framing portion and forming a gap between the cover main body and the distal framing portion; and a fragile portion, at least a part of which is provided on the annular portion of the cover main body, the fragile portion having a strength that is lower than a rest of the annular portion, and the fragile portion being broken under application of an intended stress and configured to have a user recognize breakage of the fragile portion in cooperation with the gap.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view of an endoscope according to first and second embodiments.

FIG. 2A is a schematic perspective view showing a distal framing portion of the endoscope according to the first embodiment.

FIG. 6 is a schematic perspective view showing the endoscope cover in a state of currently being attached to the distal framing portion of the endoscope according to the first embodiment.

FIG. 14A is a schematic front view showing an acting portion at one end of the jig for removing the endoscope cover from the distal framing portion of the endoscope according to the first and second embodiments.

FIG. 15B is a schematic perspective view showing the jig in a state of having been fitted onto the cover to remove the endoscope cover from the distal framing portion of the endoscope according to the first embodiment.

FIG. 16A is a schematic longitudinal sectional view showing the jig in a state of having been fitted onto the cover to remove the endoscope cover from the distal framing portion of the endoscope according to the first embodiment.

FIG. 19A is a schematic view showing the endoscope cover attached to the distal framing portion of the endoscope, in a state that the endoscope cover is disassembled, according to a modification example (first modified example) of the first embodiment.

FIG. 19B is a schematic longitudinal sectional view taken along line 19B-19B in FIG. 19A.

FIG. 27 is a schematic top view showing the endoscope cover attached to the distal framing portion of the endoscope according to the second embodiment in a state in which the fragile portion is broken by pressing with a finger the right side edge closer to the fragile portion.

DETAILED DESCRIPTION OF THE INVENTION

Figure 2B:
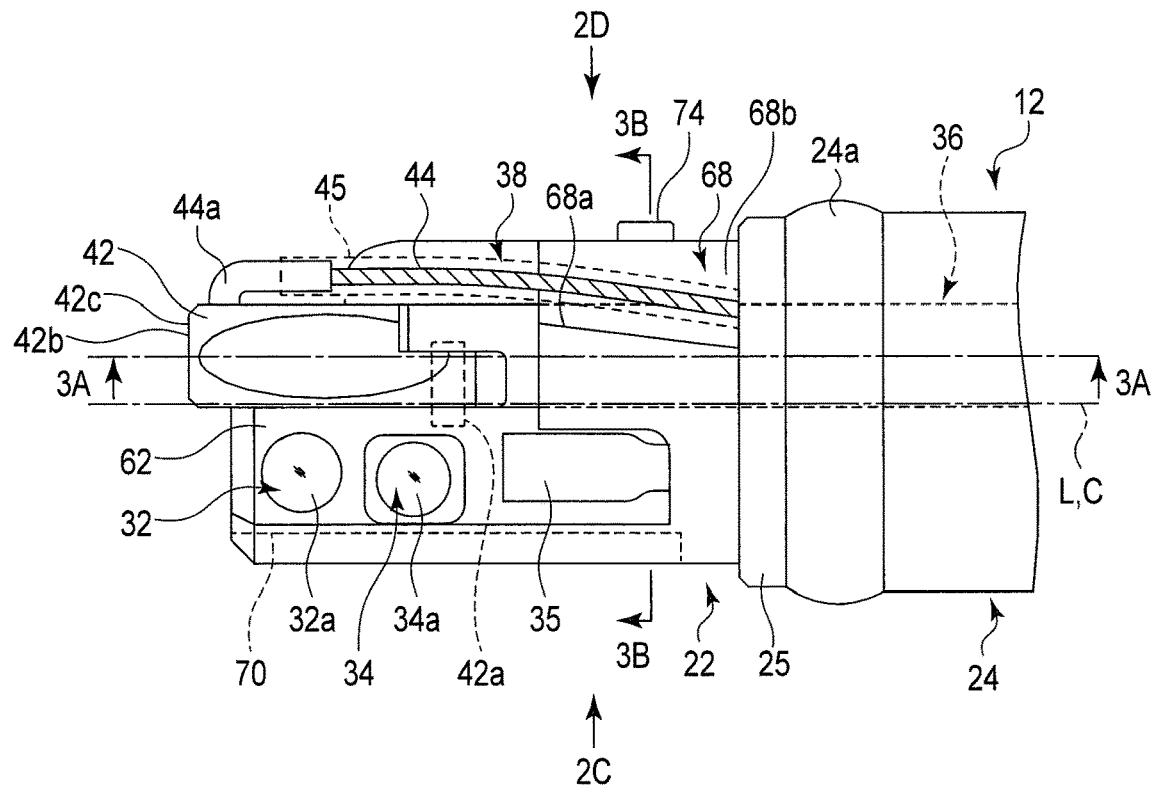
FIG. 2B is a diagram of the distal framing portion of the endoscope according to the first embodiment viewed from an arrow 2B side in FIG. 2A.
Figure 2C:
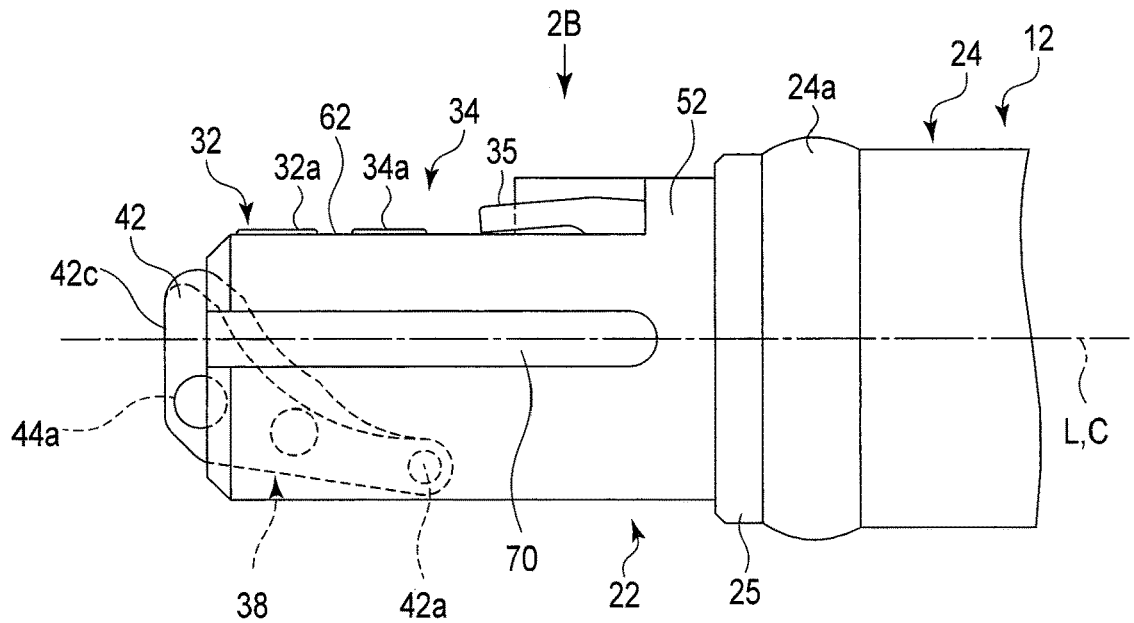
FIG. 2C is a diagram of the distal framing portion of the endoscope according to the first embodiment viewed from an arrow 2C side in FIG. 2B.
Figure 2D:
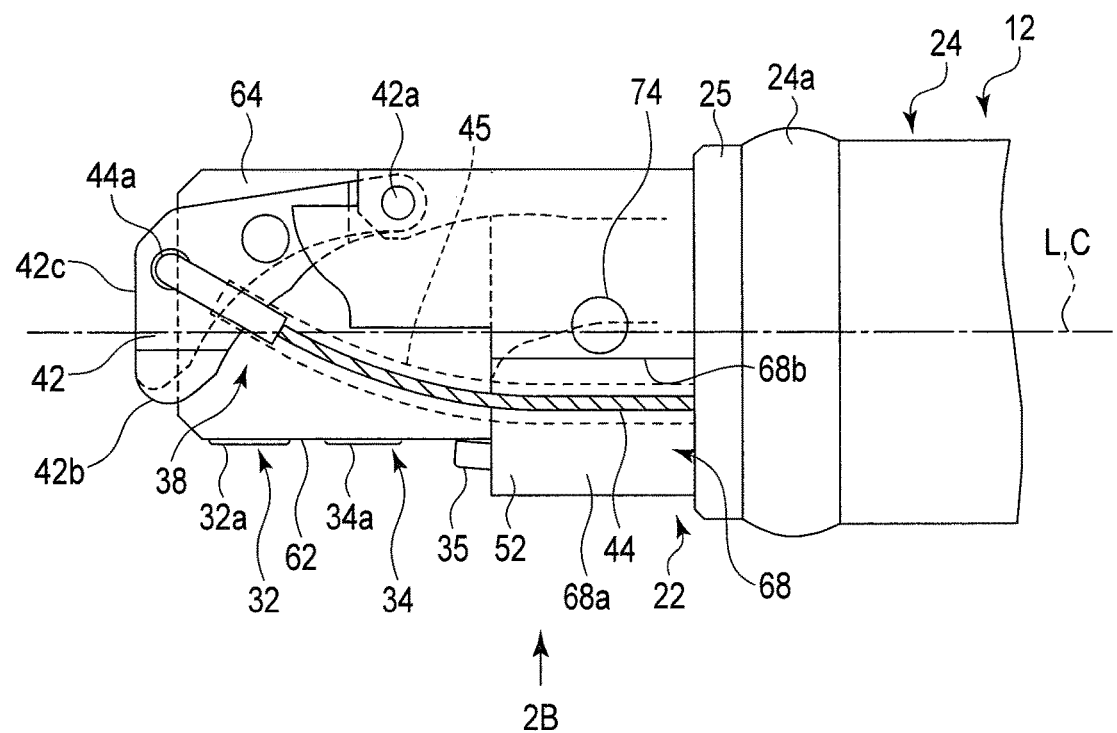
FIG. 2D is a diagram of the distal framing portion of the endoscope according to the first embodiment viewed from an arrow 2D side in FIG. 2B.

Embodiments of the present invention will be described below with reference to the drawings.

The first embodiment is described with reference to FIGS. 1 to 18B.

As shown in FIG. 1, an endoscope (insertion device) 10 according to the embodiment includes an insertion section 12 that is to be inserted into a duct such as a lumen, an endoscope cover (hereinafter mainly referred to as a cover) 14 attached to a distal end of the insertion section 12, an operation section 16 provided at a proximal end of the insertion section 12 and held by a user, and a universal cord 18 extending from the operation section 16. The cover 14 is formed to be disposable, as will be described in detail later. The cover 14 is easily attachable to a distal framing portion 22 of the insertion section 12 with the shape of the cover 14 maintained, but is configured so as not to be easily removed from the distal framing portion 22 unless at least part of the cover 14 is broken.

The insertion section 12 defines a longitudinal axis L by its distal end and proximal end. The insertion section 12 includes, in the order from the distal end to the proximal end, the distal framing portion 22, a bending portion 24, and a tubular portion 26. The tubular portion 26 may be a so-called flexible scope, which has flexibility, or may be a so-called rigid scope, which maintains a straight state and is resistant to bending. The bending portion 24 can be bent in multiple directions such as in two directions including upward and downward directions, or in four directions including upward, downward, rightward, and leftward directions in response to the operation of a knob 16a of the operation section 16, using a publicly known mechanism. An annular electrical insulation member 25 is fixed to the distal end of the bending portion 24. At a position adjacent to the proximal end side of the insulation member 25, a thread wound portion 24a, which will be described later, is provided.

The endoscope 10 is publicly known and therefore will be briefly discussed. The endoscope 10 includes an illumination optical system 32, an observation optical system 34, and a treatment instrument insertion channel 36. Additionally, the endoscope 10 includes an air/water supply mechanism and a suction mechanism that are not shown. The air/water supply mechanism includes a nozzle 35 and a tube 35a (see FIG. 8B), which are described later, at its distal end, and is operated by a button 17a provided in the operation section 16. The suction mechanism communicates with the treatment instrument insertion channel 36, and is operated by a button 17b provided in the operation section 16.

The illumination optical system 32 and the observation optical system 34 are inserted through the distal framing portion 22, the bending portion 24, and the tubular portion 26 of the insertion section 12, the operation section 16, and the universal cord 18 in the endoscope 10. The illumination optical system 32 has an illumination window 32a in the distal framing portion 22. The observation optical system 34 has an observation window 34a in the distal framing portion 22.

The channel 36 has a distal end that is open into the distal framing portion 22 of the insertion section 12 of the endoscope 10, and has a proximal end that is open in the vicinity of a proximal portion of the tubular portion 26 of the insertion section 12 or into the operation section 16. Here, as shown in FIG. 1, the operation section 16 has an opening (not shown) at the proximal end of the channel 36, and a forceps plug 36b is attachable to and detachable from this opening via a pipe sleeve. The channel 36 has a tube 36a with its distal end fixed to the distal framing portion 22 via a pipe sleeve 36c. Furthermore, the tube 36a of the channel 36 includes a suction path 36d that is publicly known, which is branched therefrom inside the operation section 16, for example. The suction path 36d is coupled to the button 17b, and when a press operation of the button 17b is performed, a suctioned object is discharged through a later-described opening 66 at the distal end of the channel 36 via the pipe sleeve 36c, the tube 36a, the suction path 36d, and the universal cord 18.

According to the present embodiment, the distal framing portion 22 is formed as a side-viewing type, in which the direction of observation differs from the direction along the longitudinal axis L of the insertion section 12. The endoscope 10 includes a swing mechanism 38, which suitably adjusts, at the distal framing portion 22, the orientation of a treatment instrument (not shown) or the like passing through the channel 36 so that the treatment target can be observed in the field of view.

The swing mechanism 38 is publicly known and therefore will be briefly discussed. The swing mechanism 38 has a distal end in the distal framing portion 22 of the insertion section 12 of the endoscope 10, and a proximal end in the operation section 16. The swing mechanism 38 includes a swing table 42, a wire 44, and a lever 46, in the order from the distal end to the proximal end of the insertion section 12. The swing table 42 is supported on the distal framing portion 22 by a support pin 42a. The distal end of the wire 44 is supported on the swing table 42, and the proximal end of the wire 44 is supported on the lever 46.

The outer periphery of the wire 44 is covered by a cylindrical wire cover 45 which is capable of being elastically deformed, and which is capable of being expanded and contracted along the axial direction of the wire 44. The distal end of the wire cover 45 is fixed to the distal end 44a of the wire 44. The proximal end of the wire cover 45 is fixed to a pipe sleeve 48, which is fixed by an O-ring 45a (see FIG. 8B) to a later-described main body 52 of the distal framing portion 22. It is preferable that the outer circumferential surface of the wire cover 45 is fixed to the main body 52 with an adhesive provided between the wire cover 45 and an opening 68d that will be described later. The distal end of the tube 48a through which the wire 44 passes is coupled to the pipe sleeve 48. The tube 48a extends toward the operation section 16, with the wire 44 inserted.

The adhesive prevents liquid and gas from penetrating the inside of the bending portion 24 and the tubular portion 26 of the insertion section 12 (see FIG. 1) along the outer periphery of the wire cover 45. Because the distal and proximal ends of the wire cover 45 are fixed, liquid and gas are prevented from penetrating the inside of the bending portion 24 and the tubular portion 26 of the insertion section 12 (see FIG. 1) along a gap between the wire 44 and the wire cover 45. Furthermore, the distal end of the wire cover 45 is movable, whereas the proximal end is not movable. This means that, when the wire 44 is pulled in the operation of the lever 46, the distal end of the wire cover 45 moves to contract the wire cover 45, and when the lever 46 releases the pulling of the wire 44, the distal end of the wire cover 45 moves back to release the contraction.

As shown in FIGS. 2A to 3B, the distal framing portion 22 includes a block-shaped main body 52. The main body 52 may be a cylindrical component of a rigid material such as stainless steel, which includes a flat portion 62, a storage portion (storage space) 64, an opening 66, a wire moving portion (wire moving region) 68, a guide groove (first guide) 70, and a pin fixing portion 72. The main body 52, which includes at least part of the outer peripheral surface of the column, defines the central axis C. For the sake of simplicity, it is assumed here that the above-described longitudinal axis L coincides with the center axis C.

The main body 52 is provided with the illumination window 32a at the distal end of an illumination optical system 32, the observation window 34a at the distal end of an observation optical system 34, the pipe sleeve 36c at the distal end of the tube 36a of the channel 36, and the swing table 42 at the distal end of the swing mechanism 38. The distal framing portion 22 is therefore constituted by the main body 52, the illumination window 32a of the illumination optical system 32, the observation window 34a of the observation optical system 34, the pipe sleeve 36c of the distal end portion of the tube 36a of the channel 36, the swing table 42 of the swing mechanism 38, the wire 44, and the wire cover 45.

Figure 3A:
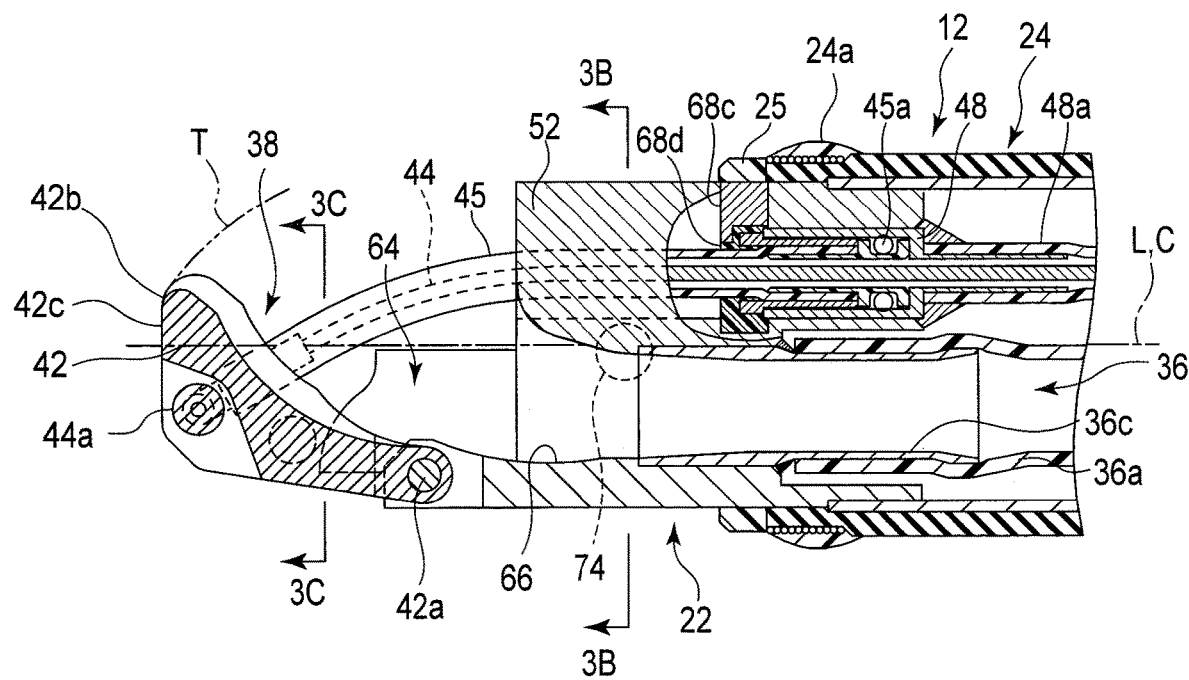
FIG. 3A is a schematic longitudinal sectional view of the distal framing portion of the endoscope according to the first embodiment, taken along the line 3A-3A in FIG. 2B.

The main body 52 includes the flat portion 62 in which the illumination window 32a and the observation window 34a are fixed, a storage portion 64 that swingably accommodates the swing table 42, and the opening 66 that communicates with the storage portion 64 to guide a treatment instrument to the swing table 42. As shown in FIG. 3A, the distal end of the tube 36a of the channel 36 is fixed to the opening 66. It is preferable that the distal end side of the storage portion 64 along the longitudinal axis L, or in other words, the distal end of the main body 52, is open. A wire moving portion 68 is formed on the proximal end side of the storage portion 64 so as to move the wire 44 and wire cover 45 continuously from the storage portion 64. The wire moving portion 68 is formed on the upper side with respect to the opening 66 in FIG. 3B. The wire moving portion 68 is positioned adjacent to the flat portion 62 in the main body 52, and is formed by a wall (wall surface) 68a, a wall (bottom surface) 68b and a wall (proximal end surface) 68c for guiding the wire 44 and wire cover 45 (see FIG. 2A). It is preferable that the walls 68a and 68b are formed as surfaces along the longitudinal axis L. The wall 68c is formed as a surface intersecting the longitudinal axis L. The walls 68a, 68b, and 68c of the wire moving portion 68 form a space (gap) with the inner peripheral surface 102a of the cover main body 102 of the cover 14, which will be described later. A gap may also be formed between the walls 68a, 68b, and 68c of the wire moving portion 68 and the proximal side edge 130 of the cover main body 102, which will be described later.

As illustrated in FIGS. 2A and 3A, the wall 68c of the wire moving portion 68 has an opening (through hole) 68d through which the wire 44 and wire cover 45 pass. It is preferable that the inner diameter of the opening 68d is formed to be equal to, or slightly smaller than, the outer diameter of the elastically deformable wire cover 45.

The flat portion 62 of the main body 52 is parallel to the longitudinal axis L. For the simplicity of explanation, the flat portion 62 is formed so that a normal N to the flat portion 62 is directed to a direction substantially orthogonal to the longitudinal axis L. Preferably, the normal N coincides with the "up" direction of the bending directions of the bending portion 24. When the up direction of the insertion section 12 is defined, and the "down", "right", and "left" directions are determined accordingly. In the flat portion 62 of the main body 52, the illumination window 32a is arranged on the distal side, and the observation window 34a is arranged on the proximal side adjacent to the illumination window 32a. The nozzle 35 is provided on the proximal side of the observation window 34a. The nozzle 35 is directed to the observation window 34a and the illumination window 32a. The nozzle 35 is configured to discharge a liquid such as physiological saline toward the observation window 34a and the illumination window 32a, and also to supply air and blow off substances adhered on the observation window 34a and the illumination window 32a.

The storage portion 64 is arranged adjacent to the flat portion 62 in a direction orthogonal to the longitudinal axis L. The storage portion 64 forms a space in which the swing table 42 can turn in a predetermined range. The swing table 42 is swingably supported on the main body 52 by the support pin 42a. When the swing table 42 is disposed at a position shown in FIGS. 2A to 3A (lowered position), a distal face 42c of the swing table 42, including distal end portion 42b, protrudes from the distal end of the main body 52 along the longitudinal axis L.

A distal end 44a of the wire 44 of the swing mechanism 38 is supported by the swing table 42. The proximal end (not shown) of the wire 44 of the swing mechanism 38 is supported by the lever 46 of the operation section 16. By adjusting the length of the wire 44, the swing table 42 is disposed at the position shown in FIGS. 2A to 3A (lowered position) with the lever 46 at a first position (i.e. when the lever 46 is raised to the maximum). As the lever 46 is pushed down, the wire 44 is pulled so that the distal end portion 42b of the swing table 42 that is provided away from the support pin 42a swings along a virtual line T shown in FIG. 3A, with the support pin 42a serving as a pivot. The lever 46 that is pushed down to the maximum is brought to a second position. At this position, the swing table 42 is disposed at a raised position where the swing table 42 is raised to the maximum.

As illustrated in FIGS. 2A to 2C, 3B, and 3C, the main body 52 of the distal framing portion 22 includes, on its outer peripheral surface, the guide groove (first restriction portion) 70 as the first guide along the longitudinal axis L. The guide groove 70 is positioned adjacent to the flat portion 62, but is separate from the storage portion 64, or in other words, separate from the wire 44 and the swing table 42 of the swing mechanism 38. It is preferable that the guide groove 70 be continuously formed from the distal end to proximal end of the main body 52.

The pin fixing portion 72 is formed on the outer peripheral surface of the main body 52 of the distal framing portion 22. It is preferable that the pin fixing portion 72 be formed adjacent to the wire moving portion 68 and on the side substantially opposite to the guide groove 70 across the central axis C of the main body 52 of the distal framing portion 22. A lock pin (lock portion) 74 protruding in the direction orthogonal to the central axis C is fixed to the pin fixing portion 72.

Figure 3B:
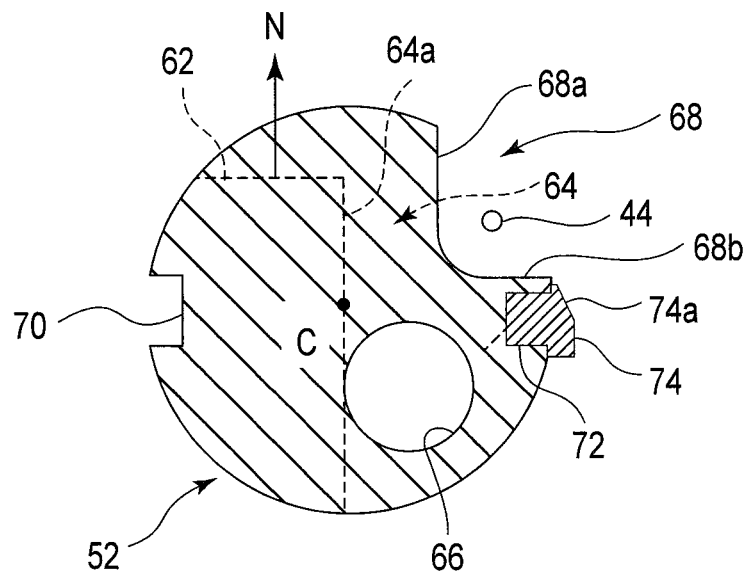
FIG. 3B is a schematic cross sectional view of the distal framing portion of the endoscope according to the first embodiment, taken along the line 3B-3B in FIG. 3A.
Figure 3C:
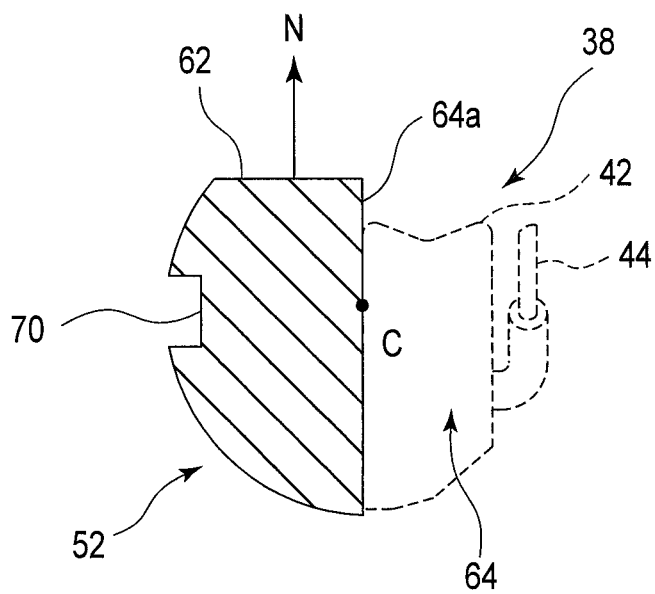
FIG. 3C is a schematic cross sectional view of the distal framing portion of the endoscope according to the first embodiment, taken along the line 3C-3C in FIG. 3A.

With respect to the wall surface 64a of the storage portion 64 shown in FIGS. 3B and 3C as a reference surface, the right side where the swing mechanism 38 is provided is referred to as a first region, and the left side including the flat portion 62 where the illumination optical system 32 and the observation optical system 34 are provided is referred to a second region. The lock pin 74 is positioned in the first region, and the guide groove (first restriction portion) 70 is positioned in the second region, separate from the lock pin 74.

It is preferable that the lock pin 74 shown in FIG. 3B include an inclined plane 74a. The inclined plane 74a is formed so that the protrusion on the side close to the wire moving portion 68 with respect to the center axis C is small, and the protrusion increases as it is farther from the wire moving portion 68.

Next, the disposable type endoscope cover 14 that is to be attached to the distal framing portion 22 is described with reference to FIGS. 4A to 5D.

Figure 4A:
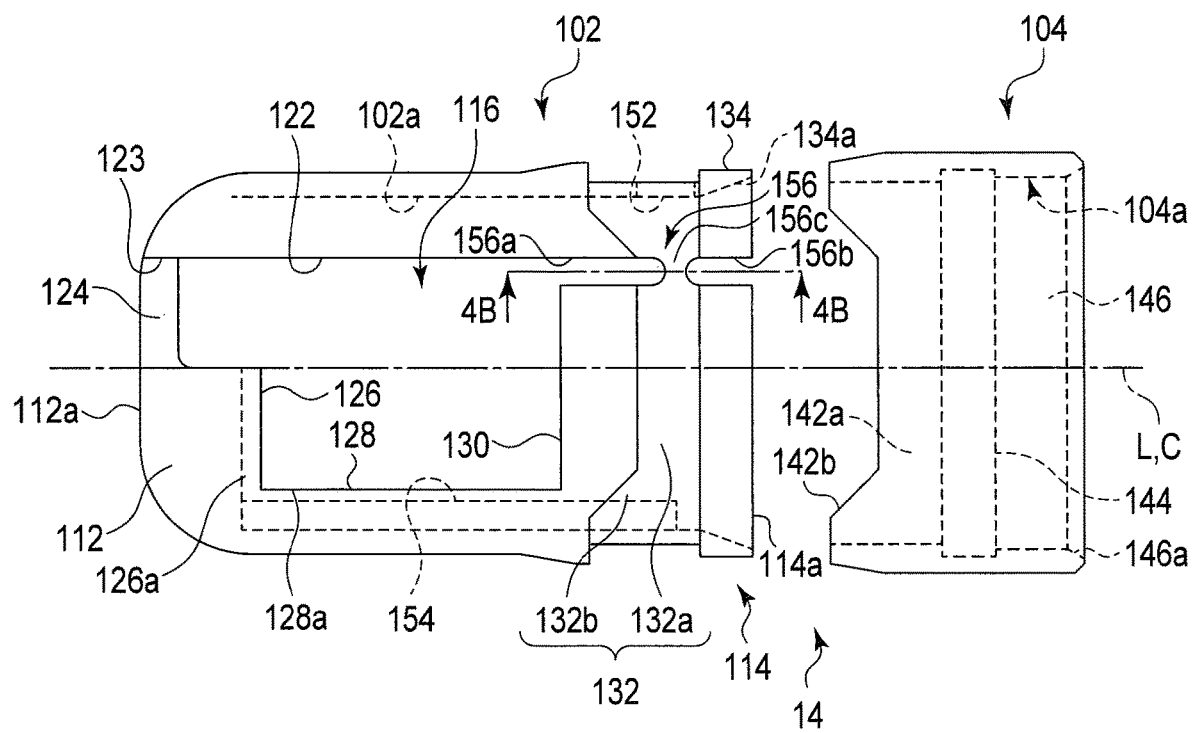
FIG. 4A is a schematic view showing an endoscope cover that is to be attached to the distal framing portion of the endoscope, in a state that the endoscope cover is disassembled, according to the first embodiment.

As shown in FIG. 4A, the endoscope cover 14 according to this embodiment includes the cover main body 102 which is to be attached to the distal framing portion 22 along the longitudinal axis L of the insertion section 12, and a presser ring 104. The cover main body 102 is integrally formed of, for example, a resin material into a cylindrical shape. The presser ring 104 is formed of, for example, a rubber material into a cylindrical shape or an annular shape. The cover main body 102 and the presser ring 104 are preferably made of an electrically insulating material. The inner diameter and inner peripheral surface 102a of the cover main body 102 and the inner diameter and inner peripheral surface 104a of the presser ring 104 are formed into suitable sizes and shapes in accordance with the size of the distal framing portion 22.

The cover main body 102 has a closed portion 112 at its distal end, and an annular portion 114 at its proximal end. The closed portion 112 is formed into a substantially semi-spherical surface. The proximal end of the cover main body 102, or in other words, the proximal end 114a of the annular portion 114, is open.

Figure 5A:
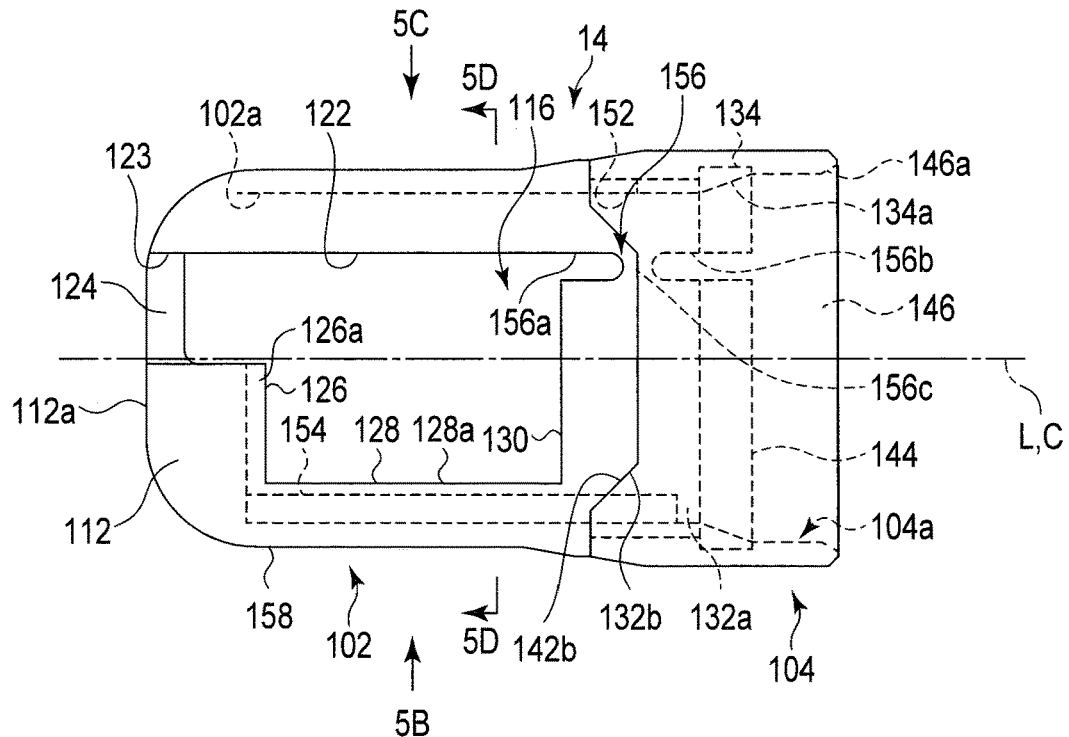
FIG. 5A is a schematic view showing the endoscope cover that is to be attached to the distal framing portion of the endoscope according to the first embodiment.
Figure 5B:
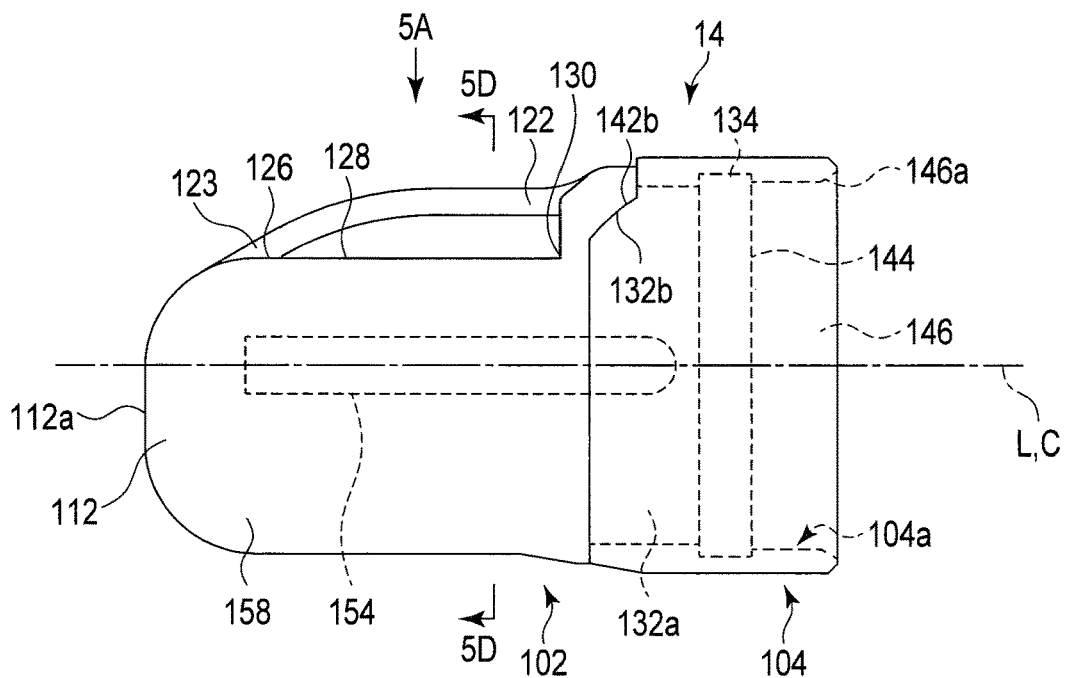
FIG. 5B is a diagram of the endoscope cover that is to be attached to the distal framing portion of the endoscope according to the first embodiment viewed from an arrow 5B side in FIG. 5A.
Figure 5C:
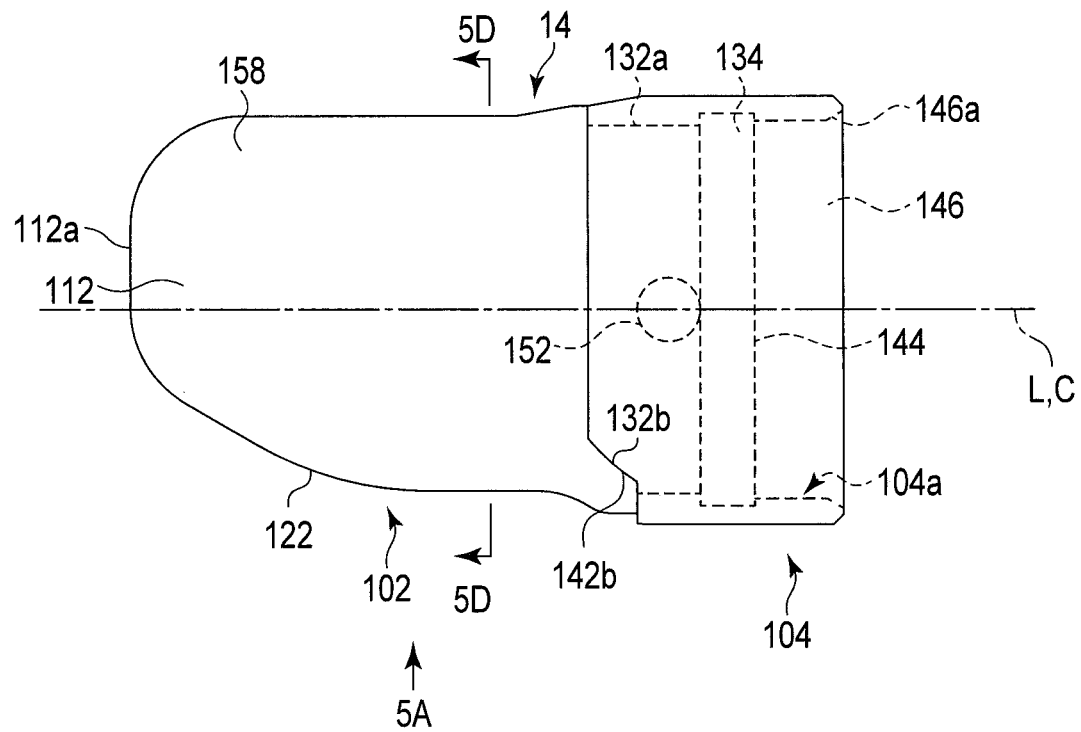
FIG. 5C is a diagram of the endoscope cover that is to be attached to the distal framing portion of the endoscope according to the first embodiment viewed from an arrow 5C side in FIG. 5A.
Figure 5D:
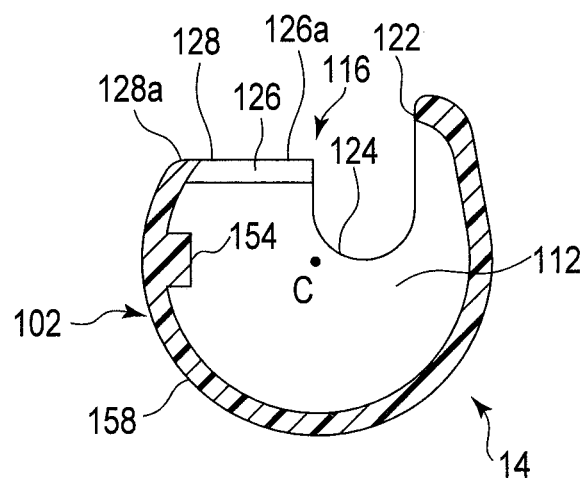
FIG. 5D is a schematic cross sectional view of the endoscope cover that is to be attached to the distal framing portion of the endoscope according to the first embodiment, taken along the line 5D-5D in FIGS. 5A to 5C.

As shown in FIG. 5D, the cover main body 102 has an open edge 116 having a substantially C-shaped cross section between the closed portion 112 and the annular portion 114. The open edge 116 is open in the direction orthogonal to the longitudinal axis L, for example. The open edge 116 exposes the illumination window 32a, the observation window 34a, the nozzle 35, and the swing table 42 of the distal framing portion 22 to the outside.

As shown in FIGS. 5A, 5B, and 5D, the open edge 116 includes a right side edge 122 on the right side of the longitudinal axis L when viewed from the proximal side to the distal side, a U-shaped depressed portion 124 continuous with the right side edge 122, a distal side edge 126 continuous with the depressed portion 124, a left side edge 128 provided continuous with the depressed portion 124 on the left side of the longitudinal axis L when viewed from the proximal side to the distal side, and a proximal side edge 130 between the right side edge 122 and the left side edge 128 on the proximal side. The open edge 116 forms a closed ring by the right side edge 122, the depressed portion 124, the distal side edge 126, the left side edge 128, and the proximal side edge 130. It is preferable that the right side edge 122 and the left side edge 128 are parallel, or substantially parallel, to each other, and that the distal side edge 126 and the proximal side edge 130 be parallel, or substantially parallel, to each other.

The right side edge 122 cooperates with the annular portion 114 and a later-described rotation peripheral surface 158 (see FIGS. 5A to 5D) to cover the wire 44 and the wire cover 45 of the swing mechanism 38 in a movable manner. The distal side edge 126 has a distal side covering portion 126a that covers the distal side of the flat portion 62 of the main body 52 with respect to the illumination window 32a. Similarly, the left side edge 128 has a left side covering portion 128a that covers the left side of the flat portion 62 of the main body 52 with respect to the illumination window 32a and the observation window 34a.

The U-shaped depressed portion 124 is formed at the distal end of the right side edge 122 continuously with the right side edge 122. The depressed portion 124 is formed to face a distal end 112a of the closed portion 112. As shown in FIGS. 5B and 5C, the portion in which the depressed portion 124 is formed is tapered toward the distal side along the longitudinal axis L.

As shown in FIG. 4A, the annular portion 114 includes, on its outer peripheral surface, an attachment portion 132 to which the presser ring 104 is fitted. The attachment portion 132 is formed circumferentially on the proximal side of the proximal side edge 130 of the open edge 116 along the longitudinal axis L, at a position away from the proximal side edge 130. The attachment portion 132 includes an annular depressed portion 132a that prevents the presser ring 104 from moving along the longitudinal axis L with respect to the cover main body 102, and an attachment depressed portion 132b that prevents the presser ring 104 from moving around the longitudinal axis L. The annular depressed portion 132a and the attachment depressed portion 132b are formed integrally and continuously with each other. The annular portion 114 has an annular flange portion 134 that is formed on the proximal end of the attachment portion 132 to protrude from the annular depressed portion 132a outwardly in a radial direction of the longitudinal axis L. Formed on the inner periphery of the flange portion 134 is a skirt portion 134a, which is configured to be thinner toward the proximal side along the longitudinal axis L. The inner diameter of the skirt portion 134a increases toward the proximal side. It is preferable that the skirt portion 134a be tapered.

It is preferable that the inner diameter of the inner peripheral surface 102a of the cover main body 102 stay constant from the vicinity of the distal ends of the right side edge 122 and the left side edge 128 of the open edge 116 to the distal end of the skirt portion 134a of the flange portion 134.

The presser ring 104 includes an annular protruding portion 142a formed in the inner peripheral surface 104a of the presser ring 104 to be to the annular depressed portion 132a, and an attachment protruding portion 142b which is to be attached to the attachment depressed portion 132b. The presser ring 104 includes an annular attachment depressed portion 144 formed in the inner peripheral surface 104a of the presser ring 104, to which the flange portion 134 is to be attached on the proximal side of the annular protruding portion 142a. In this manner, the presser ring 104 is fitted to the annular portion 114 of the cover main body 102, as shown in FIGS. 5A to 5C and 6. The presser ring 104 further includes an attachment portion 146 formed on the inner peripheral surface 104a on the proximal side of the attachment depressed portion 144 to be attached to the thread wound portion 24a at the distal end portion of the bending portion 24 and the insulation member 25 at the distal end side of the thread wound portion 24a. A skirt portion 146a that is configured to be thinner toward the proximal side along the longitudinal axis L is formed on the inner periphery of the proximal end of the attachment portion 146. The inner diameter of the skirt portion 146a increases toward the proximal side. The skirt portion 146a is preferably tapered.

As shown in FIGS. 4A, 5A, 5C, and 6, a lock depressed portion (lock portion) 152 is formed in the inner peripheral surface 102a of the annular portion 114 at the proximal end of the cover main body 102 to be engaged with the lock pin 74. That is, the lock depressed portion (lock portion) 152 engages the cover main body 102 with the distal framing portion 22. The lock depressed portion 152 may be formed in a manner that the inner peripheral surface 102a of the cover main body 102 communicates with the outer peripheral surface, or may be formed simply to be depressed in the inner peripheral surface 102a of the cover main body 102. It is preferable that the lock depressed portion 152 be formed in the annular depressed portion 132a.

A guide protruding portion (second guide) 154 is formed in the inner peripheral surface 102a of the cover main body 102 to be movable along the guide groove 70. That is, the guide protruding portion 154 protrudes inwardly from the inner peripheral surface 102a of the cover main body 102 in the radial direction. It is preferable here that the guide protruding portion 154 be formed to extend from the vicinity of the distal end to the vicinity of the proximal end of the inner peripheral surface 102a of the cover main body 102. The guide protruding portion 154 may be formed into a suitable shape, and may be formed to have substantially a rectangular cross section, as shown in FIG. 5D. Otherwise, although not shown, more than one guide protruding portion 154 may be formed and spaced apart at suitable intervals.

Figure 4B:
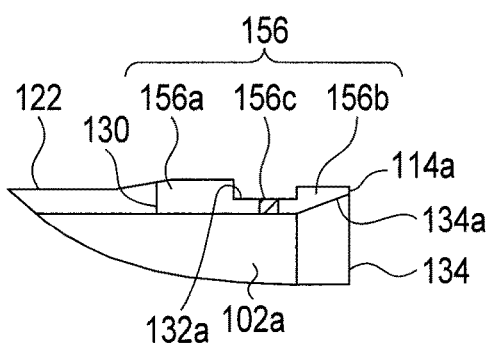
FIG. 4B is a schematic longitudinal sectional view of the endoscope cover that is to be attached to the distal framing portion of the endoscope according to the first embodiment, taken along the line 4B-4B in FIG. 4A.

As shown in FIGS. 4A and 4B, a fragile portion 156 is formed between the proximal side edge 130 of the open edge 116 of the cover main body 102 and the proximal end 114a of the flange portion 134 of the annular portion 114. The fragile portion 156 is formed to be fragile with a strength lower than the rest of adjacent portions of the annular portion 114 so as to be broken when the cover 14 is removed from the distal framing portion 22. At least part of the fragile portion 156 is positioned in the annular portion 114 of the cover main body 102 so that the annular portion 114 can be broken when intended stress is applied to the annular portion 114, and the fragile portion 156 is lower in strength than the rest of the annular portion 114. The fragile portion 156 has slits 156a and 156b. One slit 156a is formed continuously with the proximal side edge 130 of the open edge 116. The other slit 156b is formed continuously with the proximal end 114a of the flange portion 134 of the annular portion 114. The slits 156a and 156b are formed along the longitudinal axis L. The slits 156a and 156b are not communicated with each other, and a coupling portion 156c is formed between the slits 156a and 156b. Thus, the annular depressed portion 132a of the annular portion 114 is formed to be annular. The lock depressed portion 152 is formed at a position approximately 90° away from the coupling portion 156c in the peripheral direction with respect to the longitudinal axis L. The guide protruding portion 154 is formed at a position approximately 90° away from the coupling portion 156c on the side opposite to the lock depressed portion 152 in the peripheral direction of the longitudinal axis L. It is preferable that the fragile portion 156 be positioned approximately 90° away from each of the guide protruding portion 154 and the lock depressed portion 152 in the peripheral direction of the central axis C. That is, the position of the guide protruding portion 154 differs from the position of the lock depressed portion 152 in the peripheral direction with respect to the longitudinal axis L. It is further preferable that, as described later, the fragile portion 156 is positioned more than 90° away from the guide protruding portion 154 in the peripheral direction, and that the distance between the fragile portion 156 and the lock depressed portion 152 is shorter than the distance between the guide protruding portion 154 and the fragile portion 156.

The slit 156b on the proximal side contributes to the elastic deformation of the annular portion 114. That is, the flange portion 134 is elastically deformed when the engagement is established between the lock depressed portion 152 and the lock pin 74.

As shown in FIGS. 5A to 5D, the cover main body 102 has, in its outer periphery, the rotation peripheral surface 158. The rotation peripheral surface 158 is formed as part of the circular cylinder. The central axis C of the cover 14 and the distal framing portion 22 is defined by the rotation peripheral surface 158. This rotation peripheral surface 158 is fitted to a support peripheral surface 214 of a jig 200, which will be described later.

When the cover 14 is prepared, the presser ring 104 is attached to the cover main body 102 shown in FIG. 4A. First, the user checks to confirm that the coupling portion 156c is present between the slits 156a and 156b of the cover main body 102, and the slits 156a and 156b are not continuous with each other. Then, as shown in FIGS. 5A to 5C, the presser ring 104 is fitted to the cover main body 102 to obtain the cover 14.

As shown in FIG. 6, the cover 14 is attached to the distal framing portion 22 by aligning the cover 14 with the distal framing portion 22 in the peripheral direction with respect to the longitudinal axis L. The guide protruding portion 154 of the cover 14 is engaged with the guide groove 70 of the main body 52 of the distal framing portion 22, and the cover 14 is moved along the longitudinal axis L. This prevents the cover 14 from being displaced with respect to the distal framing portion 22 in the peripheral direction.

Furthermore, when the cover 14 is attached to the distal framing portion 22, the skirt portion 146a of the attachment portion 146 of the presser ring 104 of the cover 14 is in contact with the lock pin 74 of the distal framing portion 22. At this point, the attachment portion 146, which has elasticity, is elastically deformed to move on the lock pin 74. The lock pin 74 of the distal framing portion 22 is therefore brought into contact with the skirt portion 134a of the annular portion 114 of the cover main body 102. At this point, the annular portion 114 is elastically deformed by the slit 156b. As a result, the lock depressed portion 152 engages with the lock pin 74 of the distal framing portion 22. Then, the displacement of the cover 14 with respect to the distal framing portion 22 in the axial direction and in the peripheral direction can be prevented.

Figure 7:
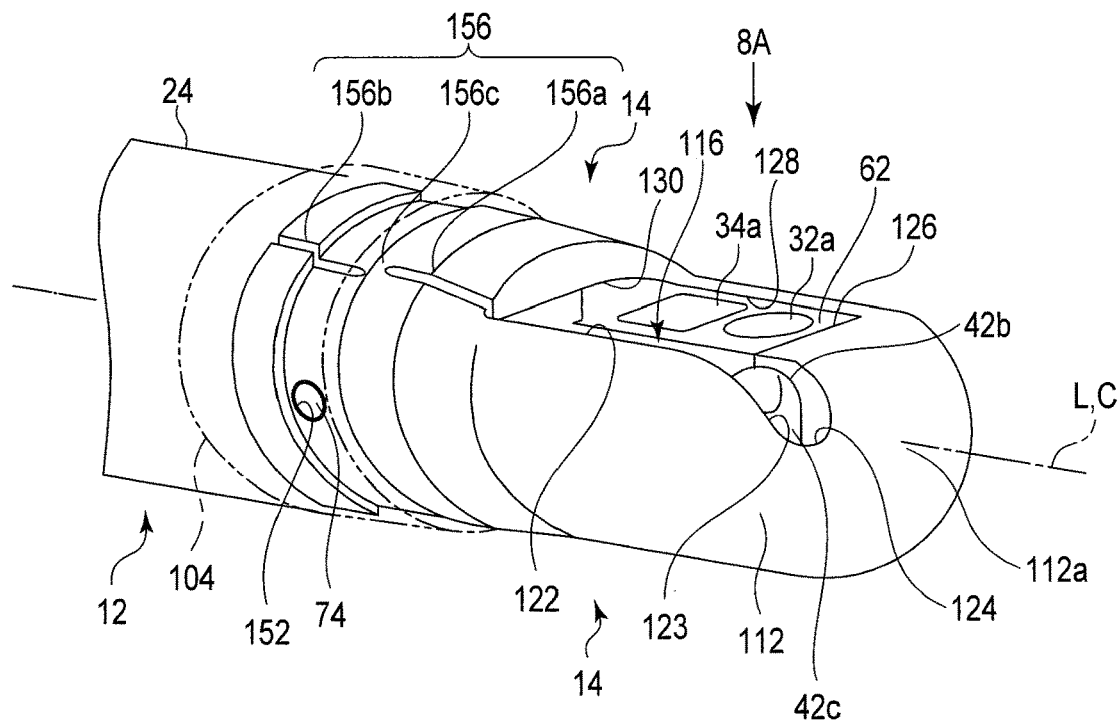
FIG. 7 is a schematic perspective view showing the endoscope cover in a state of having been attached to the distal framing portion of the endoscope according to the first embodiment.
Figure 8A:
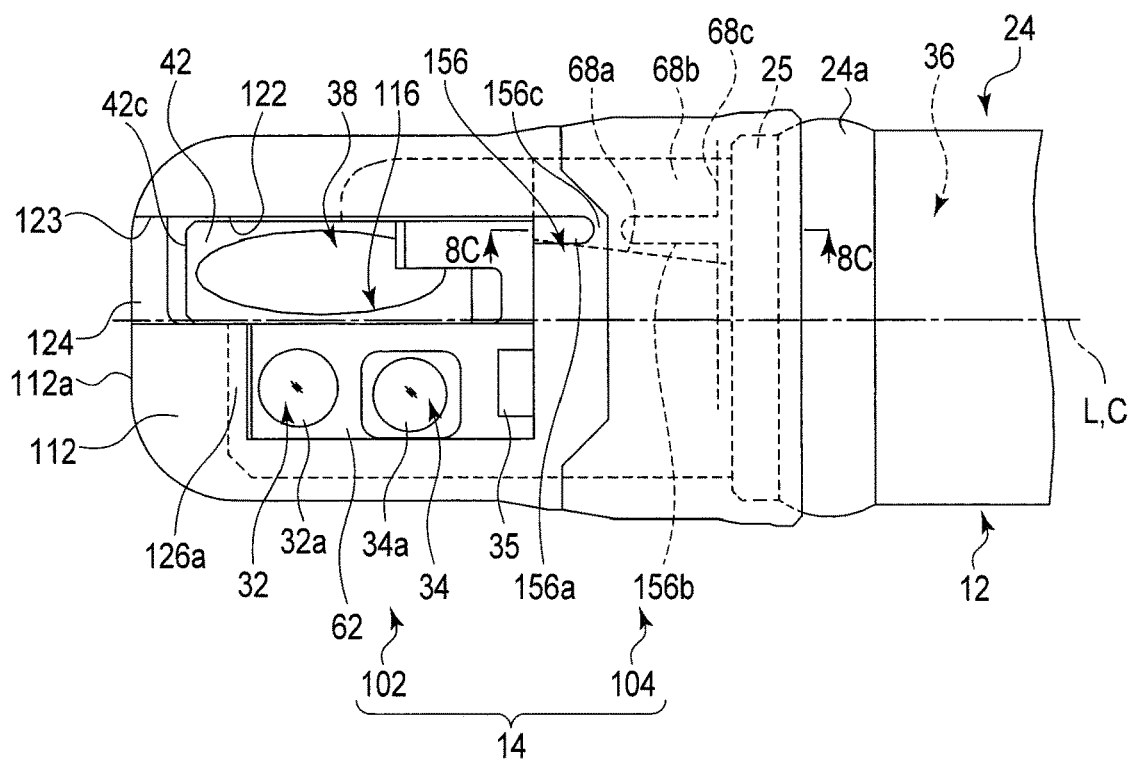
FIG. 8A is a diagram of the endoscope cover in a state of having been attached to the distal framing portion of the endoscope according to the first embodiment as viewed from an arrow 8A side in FIG. 7.
Figure 8B:
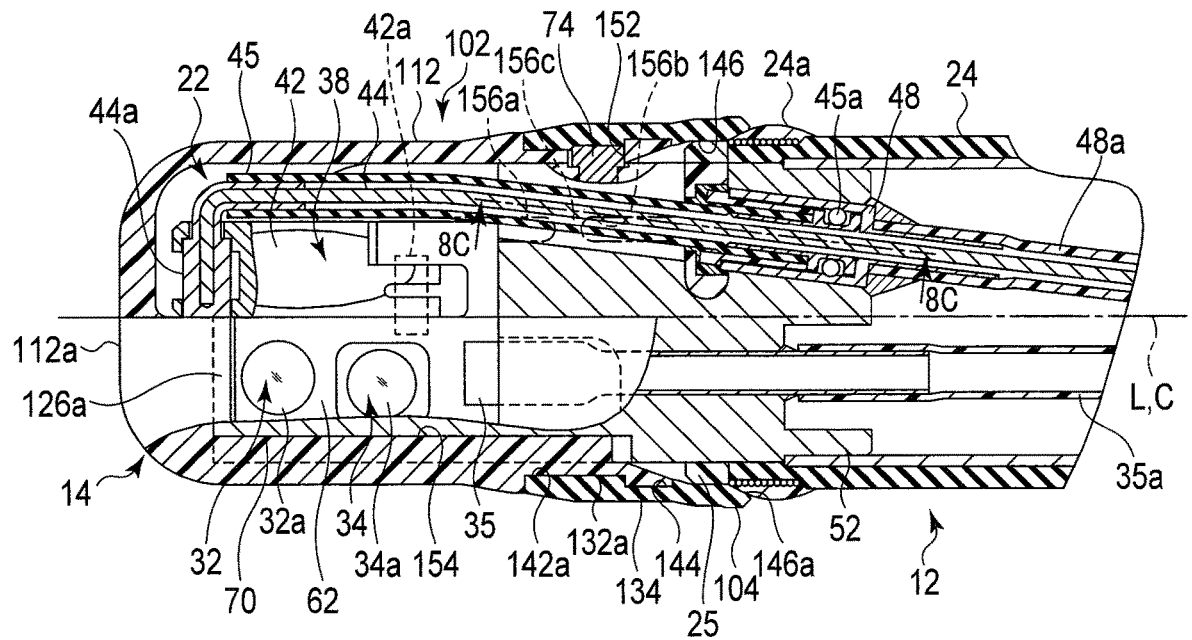
FIG. 8B is a schematic cross sectional view showing the endoscope cover in a state of having been attached to the distal framing portion of the endoscope according to the first embodiment, taken along a plane that includes a lock pin and is parallel to a plane on which the illumination window and the observation window are arranged.
Figure 8C:
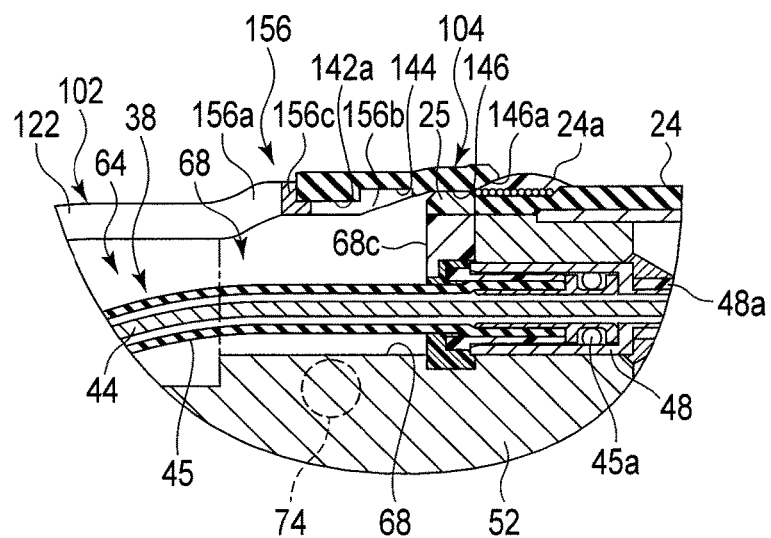
FIG. 8C is a schematic longitudinal sectional view, taken along line 8C-8C in FIGS. 8A and 8B.

As shown in FIGS. 7 to 8B, the skirt portion 146a of the attachment portion 146 of the presser ring 104 may be in contact with the thread wound portion 24a at the distal end of the bending portion 24 and/or the insulation member 25 on the distal side of the thread wound portion 24a. The inner peripheral surface of the skirt portion 146a is elastically deformed and stretched out in a radial direction outwardly from the insulation member 25 and the thread wound portion 24a. As a result, the inner peripheral surface of the skirt portion 146a is brought into tight contact with the insulation member 25 and/or the thread wound portion 24a. The thread wound portion 24a is prepared by annularly winding a thread and applying an adhesive to the outer periphery of the thread to provide an electrically insulated portion in which the applied adhesive is fixed.

Figure 9:
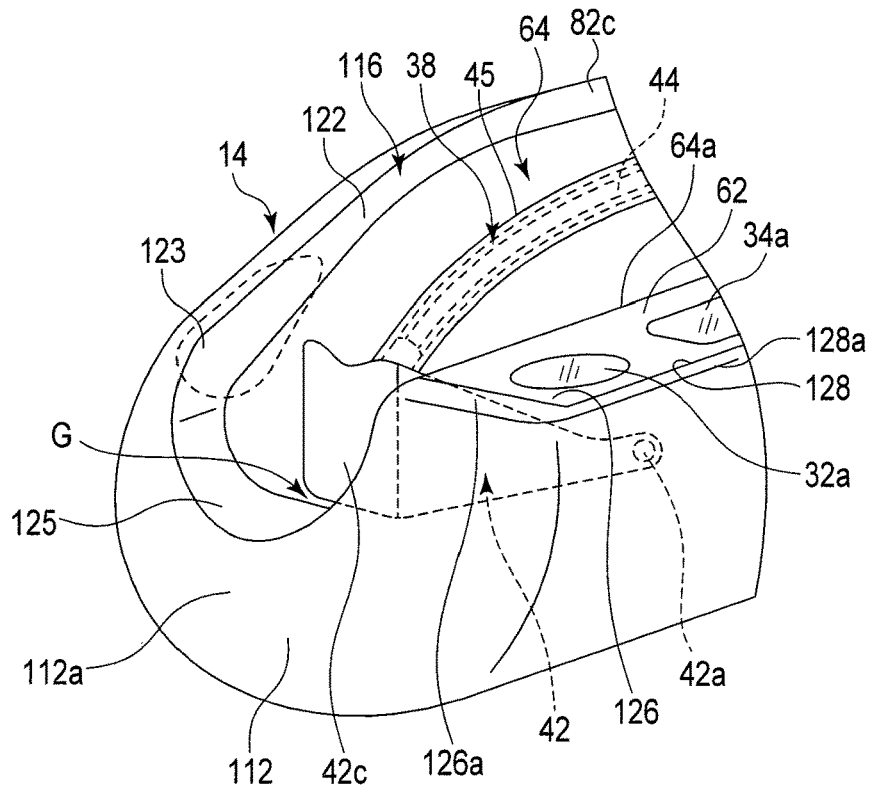
FIG. 9 is a schematic perspective view showing the vicinity of a distal portion in a state of the endoscope cover having been attached to the distal framing portion of the endoscope according to the first embodiment.

As shown in FIGS. 7 to 9, the illumination window 32a, the observation window 34a, and the nozzle 35 are exposed from the open edge 116 of the cover 14, and the swing table 42 is exposed to be swingable in a suitable range. With the cover 14 suitably attached to the distal framing portion 22, the distal end portion 42b and part of the distal face 42c of the swing table 42 are exposed when viewed from the distal side of the longitudinal axis L. Thus, when a not-shown treatment instrument is guided by the swing table 42 to protrude from the distal end of the swing table 42, the depressed portion 124 can prevent the treatment instrument from interfering with the cover 14. In addition, in order to suppress friction between the swing table 42 and the cover main body 102 that is attached to the distal framing portion 22, a gap G is provided between the swing table 42 and the cover main body 102. In particular, the gap G is formed between the distal face 42c of the swing table 42 and the depressed portion 124 of the cover 14. When the swing table 42 is swung, the volume of gap may change between the distal face 42c of the swing table 42 and the depressed portion 124 of the cover 14, but the gap is still maintained. The cover main body 102 will therefore be prevented from interfering with the motion of the swing table 42. In the cross section of the distal framing portion 22 to which the cover 14 is attached, the outer peripheral surface as indicated with a reference number 158 forms a partial ring shape.

When the cover 14 attached to the distal framing portion 22 is viewed in a section perpendicular to the longitudinal axis L and then the section is divided into the first region and the second region different from each other as defined above, the lock depressed portion 152 is located in the first region, and the guide protruding portion 154 is located in the second region.

As shown in FIGS. 8A and 8B, the fragile portion 156 is positioned not on the flat portion 62, but on the wire moving portion (wire moving region) 68 of the main body 52 of the distal framing portion 22, according to the present embodiment. In other words, the wire moving portion (wire moving region) 68 is provided inside at a position corresponding to where the fragile portion 156 of the cover main body 102 is formed. This means that the breakable coupling portion 156c of the fragile portions 156 is positioned in the same space as the wire moving portion 68.

Observation and treatment by inserting the insertion section 12 of the endoscope 10 into a duct such as a lumen is performed when the cover 14 is attached to the distal framing portion 22. It should be noted that part of the fragile portion 156 is covered and protected by the presser ring 104. For this reason, even if the fragile portion 156 hits the interior wall or the like during the insertion into a duct in a body cavity or the like, or during a treatment, the breakage of the fragile portion 156 can be avoided.

After the use of the endoscope 10, the cover 14 is removed from the distal framing portion 22. The cover main body 102 and the presser ring 104 of the cover 14 are disposed of as-is. The distal framing portion 22, from which the cover 14 is removed, is washed, disinfected, and sterilized to be reused. In other words, the endoscope 10, from which the cover 14 is removed, is washed, disinfected, and sterilized to be reused. Because the cover 14 is removed from the distal framing portion 22, washing can be readily conducted, not only for the vicinity of the illumination window 32a of the illumination optical system 32 and the observation window 34a of the observation optical system 34, but also for the channel 36 and the swing mechanism 38.

Figure 10:
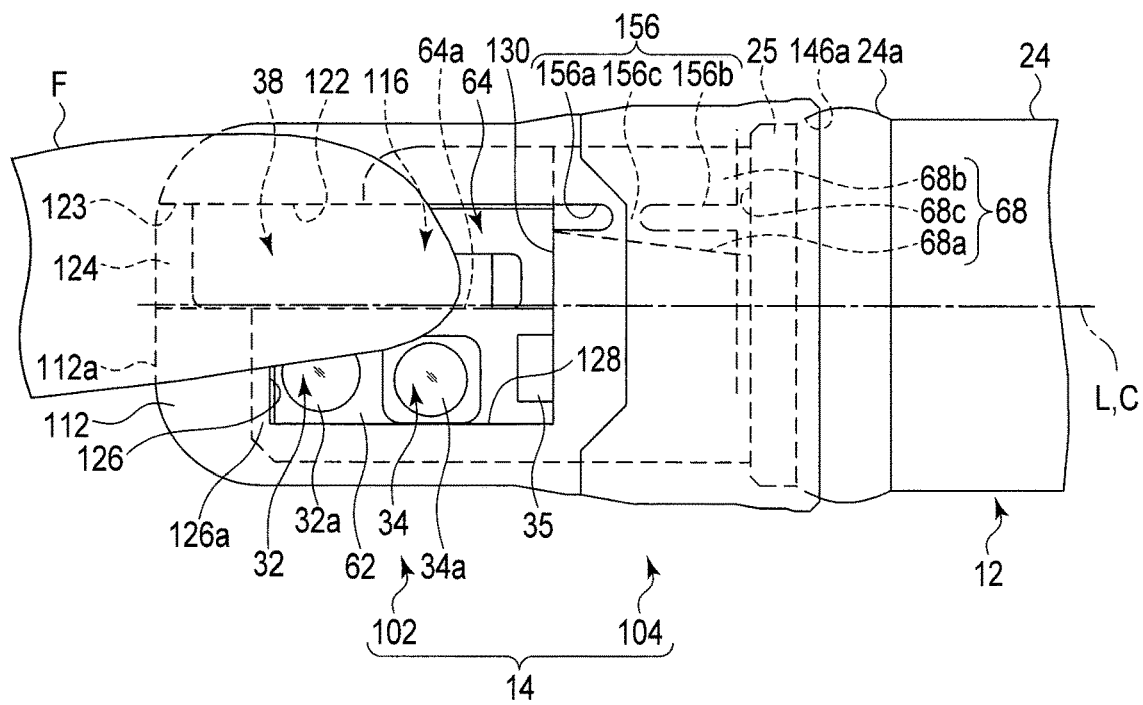
FIG. 10 is a schematic top view showing a state of breaking the fragile portion of the endoscope cover that is attached to the distal framing portion of the endoscope according to the first embodiment by pressing a pressure receiving portion at a position farther from the fragile portion with a finger.
Figure 11:
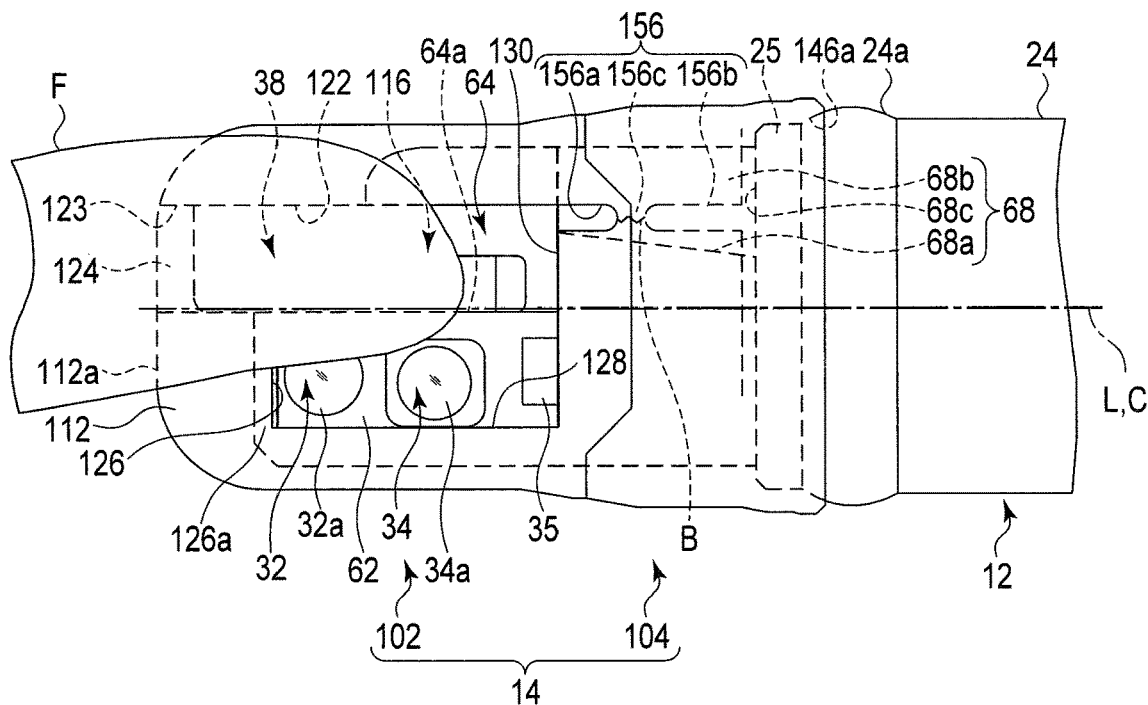
FIG. 11 is a schematic top view showing the fragile portion of the endoscope cover attached to the distal framing portion of the endoscope according to the first embodiment, in a state of having been broken by pressing the pressure receiving portion at a position farther from the fragile portion with the finger.

When the cover 14 is removed from the distal framing portion 22, the user breaks the coupling portion 156c between the slits 156a and 156b, using the force of his/her finger F, as shown in FIGS. 10 and 11, for example. The pressure receiving portion 123 shown in FIG. 9 may be pressed to spread the right side edge 122 away from the wall surface 64a of the storage portion 64. With the guide groove 70 engaged with the guide protruding portion 154, the cover 14 is prevented from being turned in the circumferential direction of the longitudinal axis L. A crack (breakage portion) B is produced in the coupling portion 156c of the fragile portion 156 in a direction orthogonal to the direction to which a breaking force is applied (i.e., the circumferential direction of the longitudinal axis L), and the coupling portion 156c is broken along the longitudinal axis L. Thus, when the coupling portion 156c of the fragile portion 156 is broken along the longitudinal axis L, the annular portion 114 is split at the slits 156a and 156b. Because the slits 156a and 156b are provided, the cut length of the fragile portion 156 of the coupling portion 156c can be set short.

With the breakage of the fragile portion 156, the engagement of the lock depressed portion 152 with the lock pin 74 of the distal framing portion 22 is released.

In accordance with the breakage portion B produced in the coupling portion 156c between the slits 156a and 156b, a breaking sound is generated. As a breaking sound, a solid propagation sound propagating through the cover 14 and an air propagation sound propagating through the air are generated. The air propagation sound of the breaking sound reflects between the inner peripheral surface 102a of the cover main body 102 and the wire moving portion 68, which includes the walls 68a, 68b, and 68c. The walls 68a, 68b, and 68c are formed into flat surfaces, of a metal material such as stainless steel, with minimal unevenness. The sound therefore tends to be reflected and is hardly absorbed in comparison with, for example, a rubber material. Thus, the walls 68a, 68b, and 68c of the wire moving portion 68 allow, together with the inner peripheral surface 102a of the cover main body 102, for reverberation of the breaking sound of the coupling portion 156c. The wire moving portion 68 of the distal framing portion 22 is spaced apart from at least part of the inner peripheral surface 102a of the cover main body 102, in particular, from the region where the fragile portion 156 is formed, to create a gap (suitable region) between the wire moving portion 68 and the peripheral surface 102a of the cover main body 102. In other words, the cover main body 102 is attached to the distal framing portion 22 so as to be positioned apart from at least part of the distal framing portion 22 and to create a gap 68 between the cover main body 102 and the distal framing portion 22. When stress is applied to the fragile portion 156, and the fragile portion 156 is broken, the fragile portion 156 allows the user to recognize that the fragile portion 156 is broken in cooperation with the gap (wire moving region) 68 of the distal framing portion 22.

A portion of the coupling portion 156c of the fragile portion 156 that is close to the slit 156a is not covered by the presser ring 104 but is exposed. With such a configuration, the user can directly visually check the breakage portion B of the fragile portion 156.

In other words, the user can directly visually check and recognize the breakage portion B of the fragile portion 156 and also can recognize the breakage portion B by hearing the breaking sound.

Figure 12:
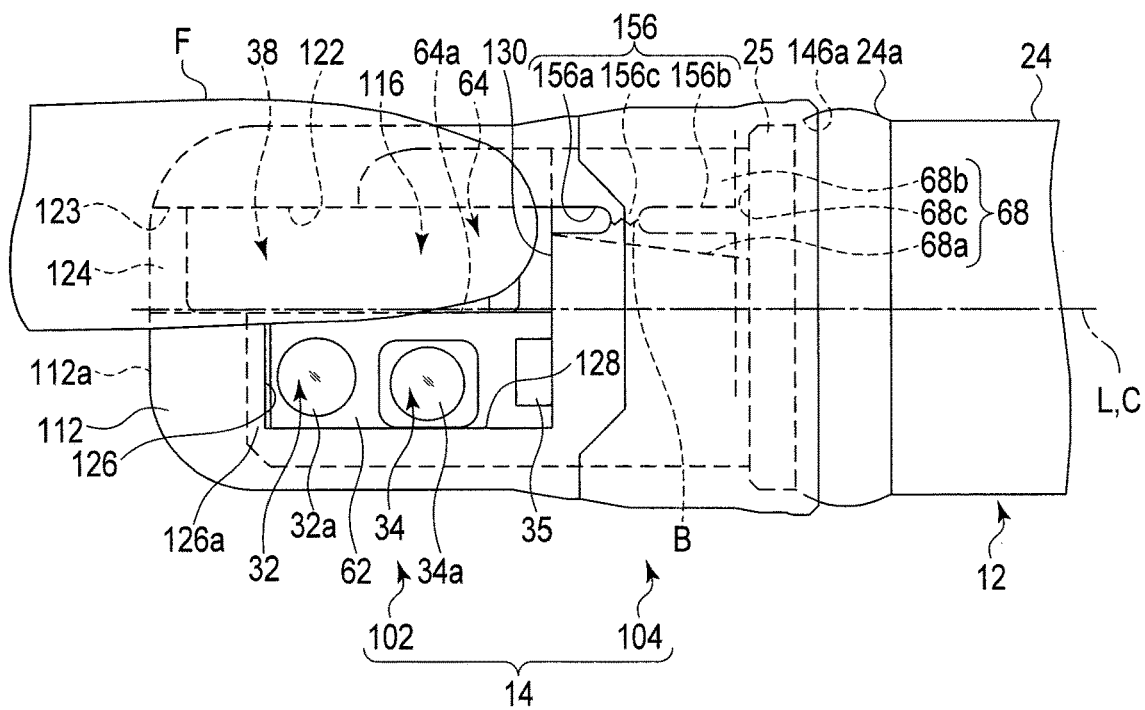
FIG. 12 is a schematic top view of the fragile portion of the endoscope cover attached to the distal framing portion of the endoscope according to the first embodiment, in a state of having been broken by pressing the right side edge at a position closer to the fragile portion with a finger.

The position of pressing the cover 14 with the finger F is not limited to the pressure receiving portion 123 shown in FIGS. 10 and 11. For example, the position of pressing the cover 14 with the finger F may be the right side edge 122 close to the fragile portion 156, as shown in FIG. 12. Pressing at this position can break the fragile portion 156 in the same manner as in FIGS. 10 and 11. When the user places the finger F at the position shown in FIG. 12 in the right side edge 122 and applies stress to break the fragile portion 156 toward the central axis C, the user can directly visually check and recognize the breakage portion B of the fragile portion 156, and also recognize the breakage portion B by hearing the breaking sound.

Furthermore, with the wire moving portion (wire moving region) 68 formed under the fragile portion 156, the coupling portion 156c may be broken by directly pressing the fragile portion 156 with the finger F. The force for breaking the fragile portion 156 may be applied in the circumferential direction of the longitudinal axis L, or in the radial direction toward the longitudinal axis L.

After breaking the fragile portion 156 and releasing the engagement of the lock depressed portion 152 with the lock pin 74 by turning the cover 14 around the central axis C with respect to the distal framing portion 22, the cover 14 can be removed by moving it toward the distal end side along the center axis C. Since the fragile portion 156 is split at the annular portion 114, the annular portion 114 of the cover main body 102 can be elastically deformed and easily stretched out.

If the fragile portion 156 is not spatially connected to the wire moving portion (wire moving region) 68, the breaking sound of the fragile portion 156 would not be reverberated. Thus, it is difficult for the user to recognize whether or not the cover 14 has been broken. In the structure, as described above, in which the wire moving portion 68 is spatially connected to the fragile portion 156, the breaking sound of the fragile portion 156 can be reverberated through the wire moving portion 68. Such a structure allows the user to recognize whether or not the fragile portion 156 has been broken, bringing the cover 14 into the state of being easily removable simply by pulling the cover 14 from the distal framing portion 22 toward the distal end side.

After the fragile portion 156 was broken, the breakage portion B will be maintained as it is, as shown in FIGS. 11 and 12. For this reason, depending on the lighting conditions, it may be difficult for the user to visually recognize the state of the broken portion B. In this case, the broken portion B may be lightly pressed so that, if it has already been broken, a sound will be generated from the broken surfaces of the breakage portion B. This sound may be caused by the broken surfaces of the breakage portion B rubbing against each other, or the broken surfaces being attached to and detached from each other. In this manner, the endoscope 10 can be inspected before being used by checking the presence or absence of a sound generated from the broken surfaces of the breakage portion B, with the cover 14 attached to the distal framing portion 22.

The fragile portion 156 is more easily deformed if the wire moving portion 68 is larger. Thus, the fragile portion 156, or in other words the targeted position can be broken more easily than the rest of the cover 14.

When the user removes the cover 14 from the distal framing portion 22 with the finger F, the position of placing the finger F may differ, as shown in FIGS. 11 and 12, and therefore the manner of removal may differ depending on the user. This may make it difficult to stably perform the breakage of the fragile portion 156. The fragile portion 156 may be reliably broken by use of the jig (removal tool for the cover 14) 200 (see FIGS. 13 to 16B) described below. It is therefore preferable that the jig 200 be used when the cover 14 is removed from the distal framing portion 22 after the use of the endoscope 10. The jig 200 may be employed for the purpose of reliably breaking the cover 14 and preventing the reuse of the cover 14.

Figure 13:
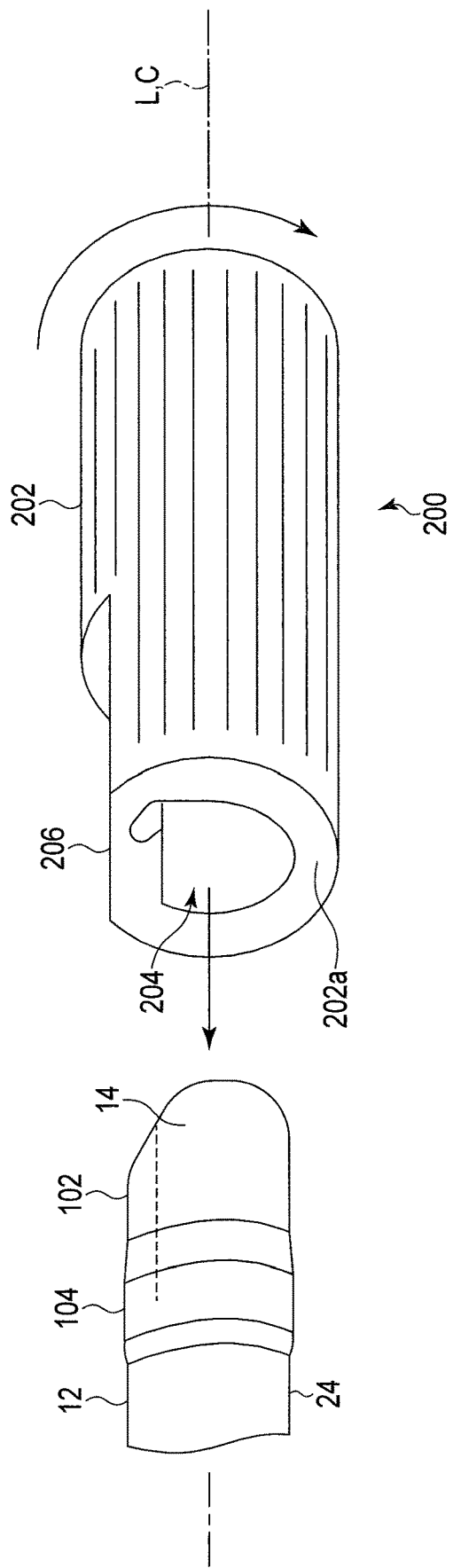
FIG. 13 is a schematic perspective view showing the endoscope cover according to the first and second embodiments in a state of currently being removed from the distal framing portion of the endoscope by use of a jig.
Figure 14B:
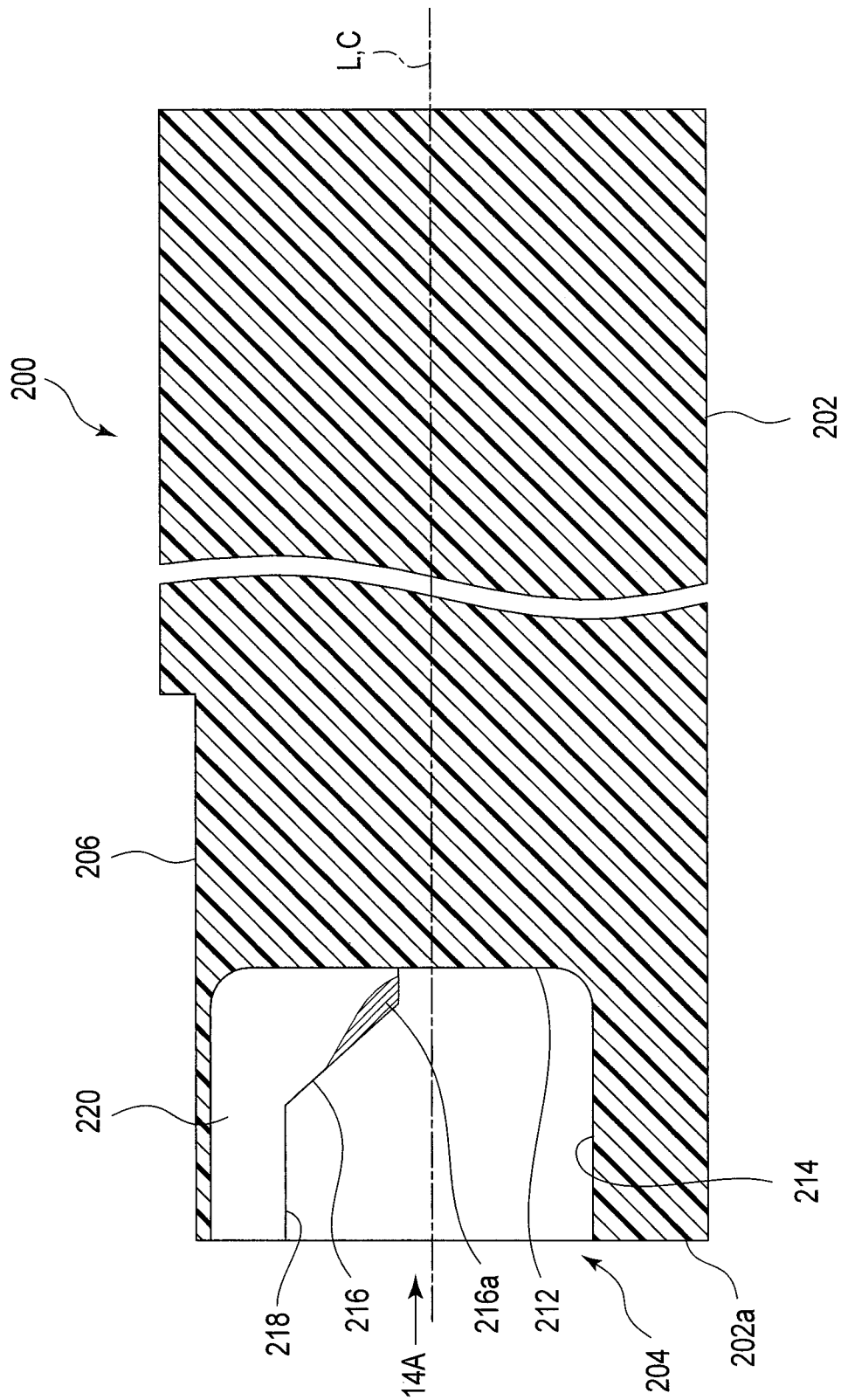
FIG. 14B is a schematic longitudinal sectional view of the acting portion at one end of the jig for removing the endoscope cover from the distal framing portion of the endoscope according to the first and second embodiments, taken along the line 14B-14B in FIG. 14A.

The cover removal jig 200 according to the present embodiment is made of a rigid material such as a resin material that is more rigid than the cover main body 102 of the cover 14, or made of a metallic material. As shown in FIG. 13, the jig 200 has a column 202. An outer periphery of the column 202 is formed into a suitable shape. As shown in FIGS. 14A and 14B, an acting portion 204, which acts on the cover 14 when removing the cover 14 attached to the distal framing portion 22, is formed at one end 202a of the column 202. The acting portion 204 is shaped into a depression which covers the vicinity of the distal end 112a of the closed portion 112 of the cover 14. An index 206, which allows the user to recognize the direction of the jig 200 in the peripheral direction around the longitudinal axis L, is formed on the outer peripheral surface of the column 202. Here, the index 206 is formed into a plane such that the direction can be recognized when the index 206 is touched. It is preferable that the index 206 be formed at a position adjacent to the acting portion 204.

The index 206 allows the user to visually check and recognize, for example, the position to insert the distal framing portion 22 to which the endoscope cover 14 is attached. The index may be letters such as "up", or may be an arrow imprinted to indicate the rotation direction. The outer shape of the cover removal jig 200 is not specifically limited.

As shown in FIGS. 14A and 14B, the acting portion 204 has a bottom surface 212, a support peripheral surface 214 that is preferably orthogonal to the bottom surface 212, a first protruding portion 216 that is fitted to the U-shaped depressed portion 124 of the open edge 116 of the cover 14, a second protruding portion 218 that is fitted to the distal side covering portion 126a of the cover 14, and a retraction portion 220 into which part of the right side edge 122 of the open edge 116 of the broken cover 14 is retracted.

Figure 15A:
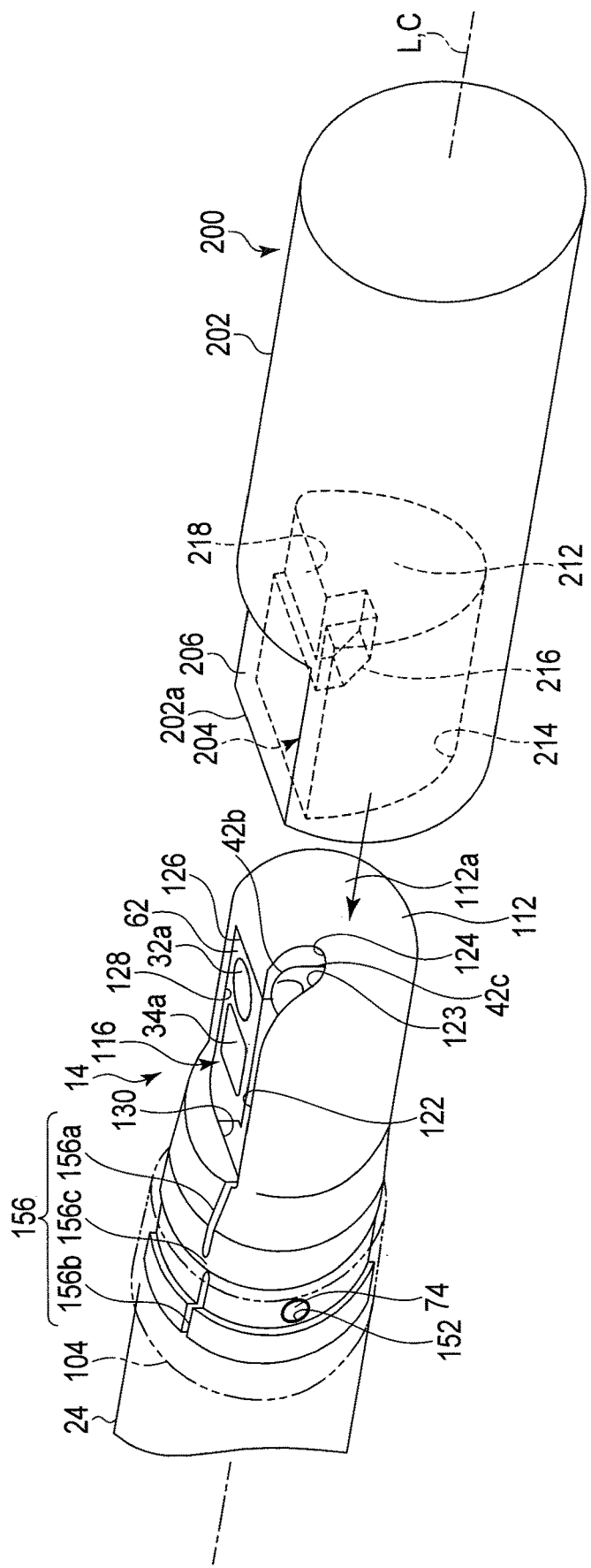
FIG. 15A is a schematic perspective view showing the jig currently being fitted onto the endoscope cover to remove the endoscope cover from the distal framing portion of the endoscope according to the first embodiment.

As shown in FIGS. 15A and 15B, the acting portion 204 at the one end 202a of the column 202 of the jig 200 is fitted to the distal framing portion 22 with the endoscope cover 14 attached.

As shown in FIG. 16A, the distal end 112a of the closed portion 112 of the cover 14 is brought into contact with the bottom surface 212. Thus, the bottom surface 212 regulates the length of the cover 14 to be inserted in the depressed acting portion 204 from the one end 202a of the jig 200, to be a certain length.

Figure 16B:
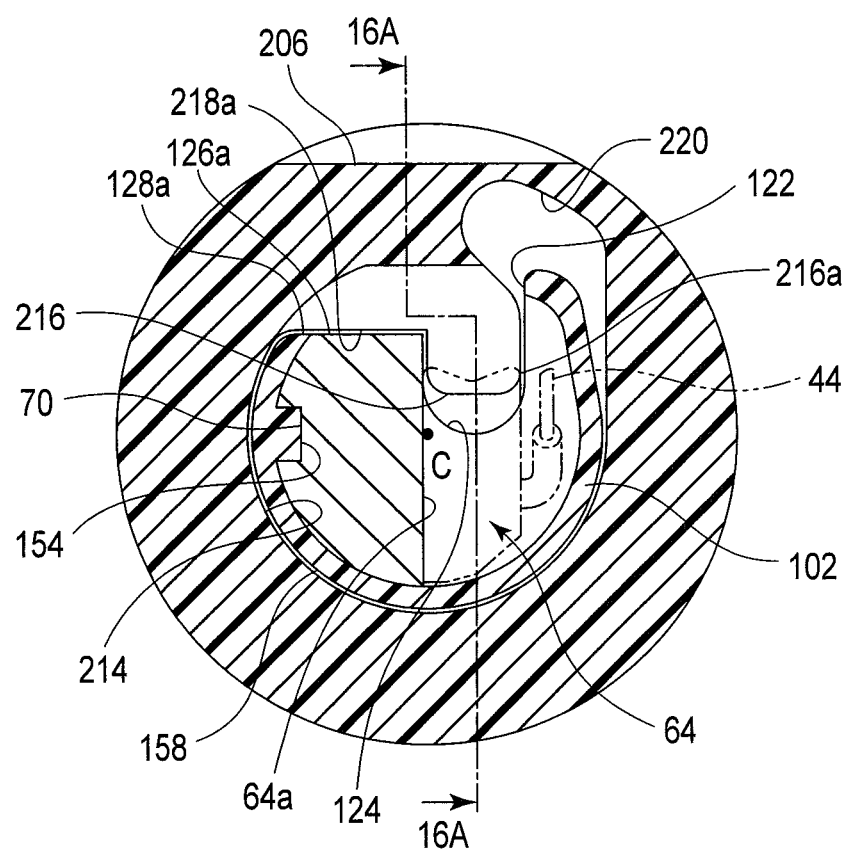
FIG. 16B is a schematic cross sectional view taken along the line 16B-16B in FIG. 16A.

As shown in FIGS. 16A and 16B, the support peripheral surface 214 is formed as a part of the circular form. The central axis C of the acting portion 204 is defined by the support peripheral surface 214. The distance between the central axis C and the support peripheral surface 214, or in other words the radius of the acting portion 204, is formed to be slightly larger than the radius defined by the rotation peripheral surface 158, which forms a part of the circular cylinder of the cover 14. The rotation peripheral surface 158 of the cover 14 therefore abuts on and is thus supported by, the support peripheral surface 214. At this point, the support peripheral surface 214 is movable relative to the rotation peripheral surface 158 around the central axis C.

As shown in FIGS. 14A and 16A, the first protruding portion 216 protrudes from the bottom surface 212 toward the one end 202a of the jig 200. The amount of protrusion of the first protruding portion 216 from the bottom surface 212 is adjusted so that, when the distal end 112a of the closed portion 112 of the cover 14 is in contact with the bottom surface 212, the first protruding portion 216 is able to be brought into contact with the depressed portion 124 of the cover 14 and is positioned separate from the distal end portion 42b and the distal face 42c of the swing table 42. Even if the swing table 42 is swung with the distal end 112a of the closed portion 112 of the cover 14 being in contact with the bottom surface 212, the first protruding portion 216 will not be brought into contact with the distal end portion 42b and the distal face 42c of the swing table 42. Moreover, the width of the first protruding portion 216 is determined to be slightly smaller than the width of the depressed portion 124 of the cover 14. Thus, the first protruding portion 216 of the jig 200 is provided with a pressure portion 216a which is brought into contact with the pressure receiving portion 123 provided between the depressed portion 124 and the right side edge 122 of the open edge 116 of the cover 14 (see FIG. 9) when the jig 200 is turned with respect to the cover 14 in the peripheral direction of the central axis C.

The second protruding portion 218 shown in FIG. 14A protrudes toward the one end 202a of the column 202 from the bottom surface 212. The second protruding portion 218 is adjacent to the first protruding portion 216 in the peripheral direction of the central axis C. The second protruding portion 218 has an opposed surface 218a, which is preferably parallel to the distal side covering portion 126a. The opposed surface 218a may be in contact with the distal side covering portion 126a of the distal side edge 126 of the cover 14. The opposed surface 218a therefore may indirectly hold the flat portion 62 of the main body 52 of the distal framing portion 22.

The use of the jig 200 for removing the cover 14 attached to the distal framing portion 22 will be explained below.

As shown in FIGS. 13 and 15A, the acting portion 204 of the jig 200 is opposed to the distal framing portion 22 with the cover 14 attached. The orientation of the index 206 is determined to be parallel to the flat portion 62 of the distal framing portion 22. In this state, the acting portion 204 of the jig 200 is fitted onto the cover 14, as shown in FIG. 15B. The central axis C of the support peripheral surface 214 of the jig 200 should be aligned with the central axis C of the rotation peripheral surface 158 of the cover 14, and the distal end 112a of the closed portion 112 of the cover 14 should be brought into contact with the bottom surface 212 of the acting portion 204 of the jig 200.

At this point, the first protruding portion 216 of the jig 200 is fitted into the depressed portion 124 of the open edge 116 of the cover 14, as shown in FIGS. 16A and 16B. The second protruding portion 218 of the jig 200 is brought close to, or in contact with, the distal side covering portion 126a of the cover 14. The second protruding portion 218 presses the cover 14 at the position close to the distal side edge 126 between the distal side edge 126 and the distal end 112a of the closed portion 112.

A gap X is created between the first protruding portion 216 and the swing table 42 (i.e., there is a distance between the first protruding portion 216 and the distal end portion 42b of the swing table 42 in FIGS. 14A to 15A), no matter where the swing table 42 is positioned by swinging. For this reason, the swing table 42 would not be brought in contact with the jig 200, at any position within a swingable range.

The jig 200 is turned with respect to the distal framing portion 22 and the cover 14 in a direction indicated by an arrow R in FIG. 15B, with the distal framing portion 22 or the vicinity of the distal portion of the insertion section 12 being held and the distal end 112a of the closed portion 112 of the cover 14 being in contact with the bottom surface 212 of the jig 200. In other words, the support peripheral surface 214 of the jig 200 that shares the central axis C with the rotation peripheral surface 158 of the cover 14 is turned around the central axis C.

Figure 16C:
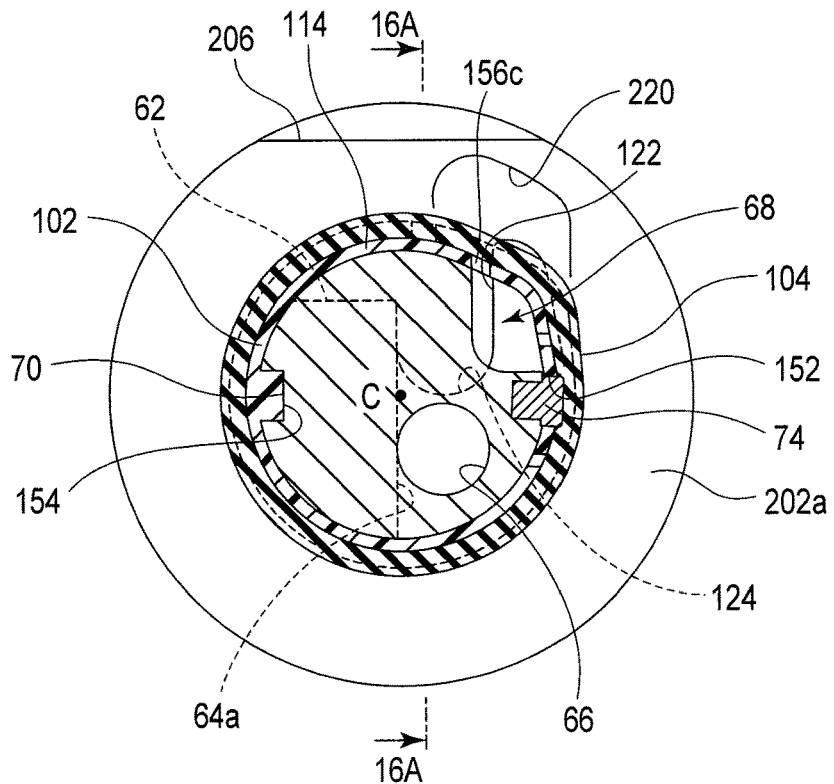
FIG. 16C is a schematic cross sectional view taken along the line 16C-16C in FIG. 16A.
Figure 16D:
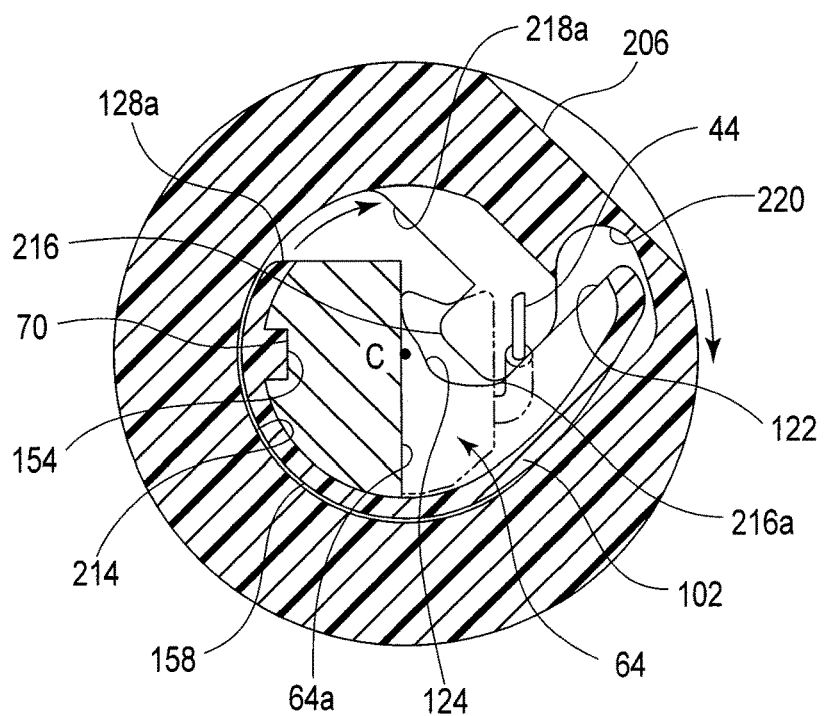
FIG. 16D is a schematic cross sectional view showing the jig fitted onto the cover, in a state of turning the jig with respect to the cover from the state shown in FIG. 16B and pressing the right side edge of an open edge to spread open a depressed portion.

As shown in FIGS. 16B and 16D, the pressure receiving portion 123 provided between the right side edge 122 and the depressed portion 124 of the open edge 116 (see FIG. 9) is being pressed by the pressure portion 216a of the first protruding portion 216, while the opposed surface 218a of the second protruding portion 218 of the jig 200 is being moved away from the distal side covering portion 126a of the cover 14.

Here, the bearing force of the guide protruding portion (second retention portion) 154 of the cover 14 is determined so that the bearing force is greater than the total of the amount of force that would break the fragile portion 156 and the amount of force that would release the engagement of the lock depressed portion 152 with the lock pin 74 when the force is applied to the cover main body 102 around the central axis C with the cover main body 102 attached to the distal framing portion 22. In other words, the guide protruding portion 154 of the cover 14 tries to maintain the engagement with the guide groove 70 of the distal framing portion 22. Thus, the guide protruding portion (second retention portion) 154 regulates the movement of the cover main body 102 with respect to the distal framing portion 22 around the central axis C.

Figure 16E:
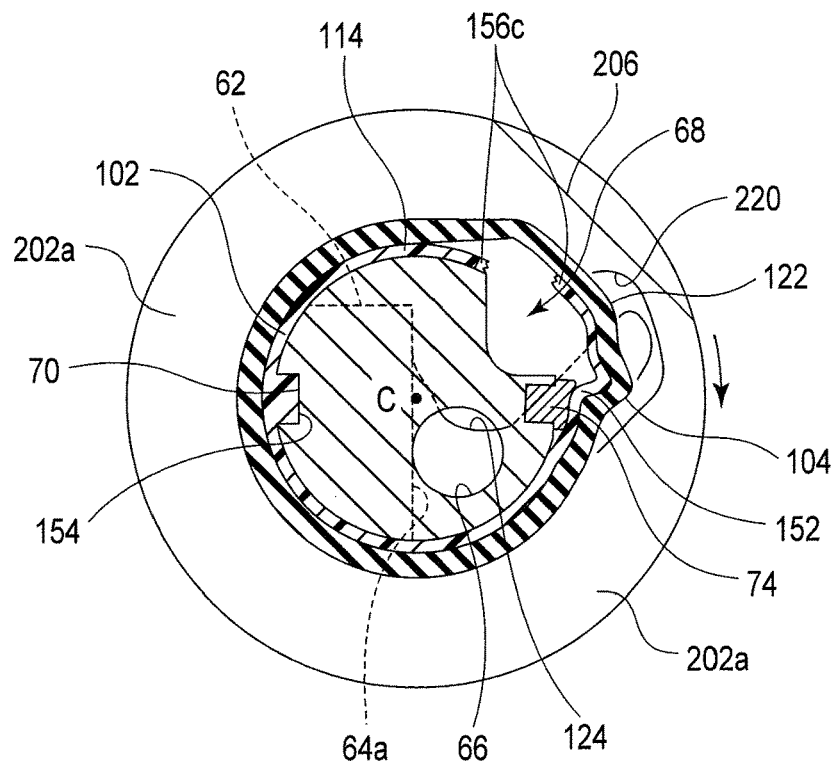
FIG. 16E is a schematic cross sectional view showing the jig fitted onto the cover in a state of turning the jig with respect to the cover from the state shown in FIG. 16C and pressing the right edge of the opening edge to spread open the depressed portion, thereby breaking a coupling portion of the fragile portion.

As shown in FIGS. 16C and 16E, the operation force of the jig 200 is applied to the coupling portion 156c between the slits 156a and 156b of the cover 14 facing the first protruding portion 216 of the jig 200 via the pressure receiving portion 123, the right side edge 122, and the proximal side edge 130, as a result of which the coupling portion 156c is broken. Due to the breakage of the coupling portion 156c, part of the attachment portion 132 of the annular portion 114 including the lock depressed portion 152 moves in the peripheral direction, while the engagement of the guide protruding portion 154 of the cover 14 with the guide groove 70 of the distal framing portion 22 is maintained. In conjunction with the breakage of the coupling portion 156c, the engagement of the lock depressed portion 152 with the lock pin 74 is released.

The inclined plane 74a of the lock pin 74 is provided on the side close to the coupling portion 156c. With the structure having such an inclined plane 74a, the lock depressed portion 152 slips along the inclined plane 74a with the momentum of the coupling portion 156c that is being broken. The engagement of the lock depressed portion 152 with the lock pin 74 therefore can be easily released with the inclined plane 74a.

Furthermore, due to the momentum of the breakage, the broken end of the coupling portion 156c moves away from the wire cover 45 that covers the wire 44, and will not move in the direction approaching the wire cover 45. Thus, the broken end portion (one of the broken surfaces) of the coupling portion 156c is prevented from applying a load onto the wire cover 45. In other words, the breakage of the coupling portion 156c will not damage the wire cover 45.

In addition, as shown in FIGS. 16C and 16E, the right side edge 122 is retracted into the retraction portion 220 of the jig 200. If the jig 200 is further turned with respect to the distal framing portion 22 and the cover 14 in the direction indicated by the arrow R in FIG. 15B, the user of the jig 200 needs to apply a force which would fold the right side edge 122. The support peripheral surface 214 of the jig 200 will then become resistant to sliding on the rotation peripheral surface 158 of the cover 14 around the central axis C. The user of the jig 200 will recognize this state. Thus, when the jig 200 is turned with respect to the distal framing portion 22 and the cover 14 in the direction indicated by the arrow R in FIG. 15B, the user of the jig 200 perceives a drag until the coupling portion 156c of the fragile portion 156 is broken and the engagement of the lock pin 74 and the lock depressed portion 152 is released. Thereafter, the user perceives reduction of the drag, and then the user perceives the drag again.

The first protruding portion 216 and the second protruding portion 218 are not in contact with any component of the distal framing portion 22. This prevents a load from being applied onto the distal framing portion 22 when the cover 14 is removed from the distal framing portion 22 by the jig 200. That is, when removing the cover 14 from the distal framing portion 22 with the jig 200, the distal framing portion 22 will not be damaged.

The fragile portion 156 is exposed, as shown in FIG. 15B, when the jig 200 is fitted to the cover 14 that is attached to the distal framing portion 22. That is, the jig 200 does not cover the fragile portion 156 and the lock depressed portion 152. This allows the user to directly observe the state of the fragile portion 156 being broken. Moreover, when the fragile portion 156 is broken by the jig 200 and the lock pin 74 is disengaged from the lock depressed portion 152, these portions are prevented from interfering with the jig 200 and from interrupting the turn and breakage operation of the jig 200.

Figure 17:
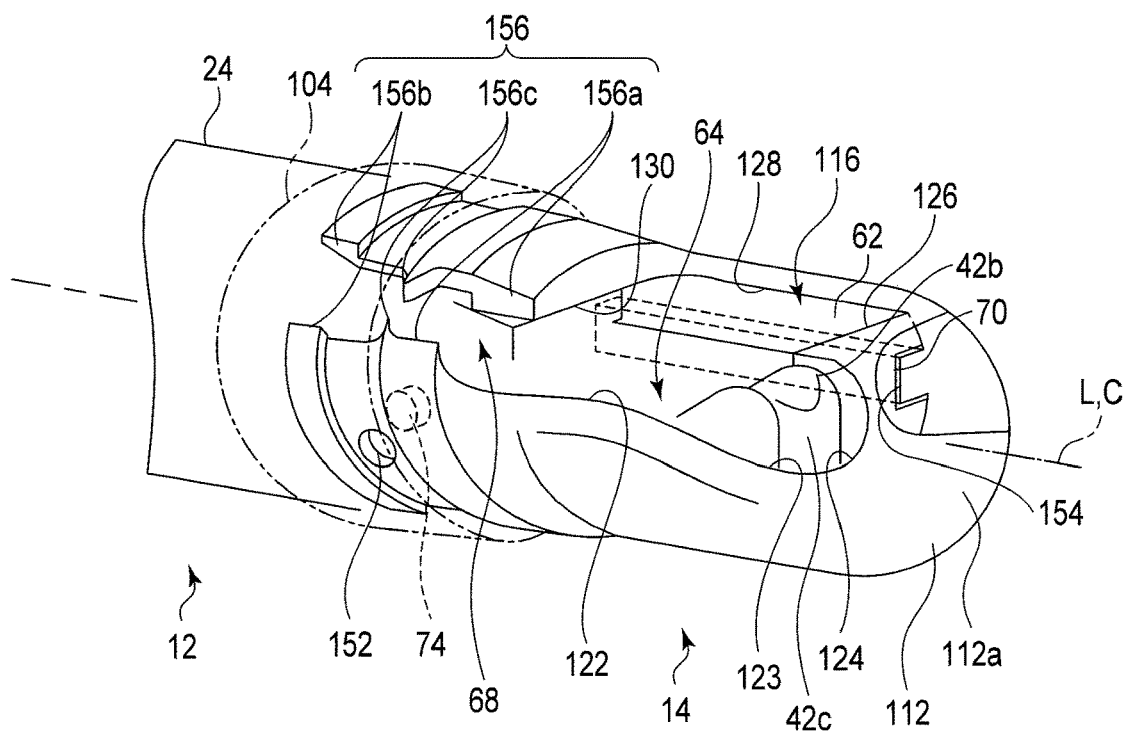
FIG. 17 is a schematic perspective view showing the endoscope cover in a state in which the coupling portion of the fragile portion is broken to remove the endoscope cover from the distal framing portion of the endoscope according to the first embodiment.

Then, as shown in FIG. 17, the jig 200 is pulled to the distal side along the longitudinal axis L from the cover 14 in which the fragile portion 156 is broken. Since the fragile portion 156 is broken and the lock depressed portion 152 is disengaged from the lock pin 74 of the distal framing portion 22, the cover 14 may be pinched by the user's fingers, or by a forceps or the like to remove the cover 14 from the distal framing portion 22 to the distal side along the longitudinal axis L. The cover 14 can be easily removed by the jig 200, while sanitation and safety is ensured for users (surgeons and surgical staff).

Depending on the conditions of the breakage, the cover 14 may come off the distal framing portion 22 together with the jig 200.

The removed cover 14 is disposed of. The endoscope, from which the cover 14 has been removed, that is, the insertion section 12 including the distal framing portion 22, the operation section 16, and the universal cord 18, are adequately washed, disinfected, and sterilized, and provided for reuse. A new cover 14 is suitably attached to the distal framing portion 22 for observation and treatment.

The jig 200 used for removal of the cover 14 from the distal framing portion 22 may be disposed of, together with the cover 14. In this case, the cover 14 and the jig 200 may be commercially offered in packages as a cover unit. Furthermore, the endoscope 10 including the cover 14 and the jig 200 may be commercially offered in packages as an endoscope unit.

If the jig 200 holding the distal framing portion 22 is turned with respect to the distal framing portion 22 and the cover 14 in a direction opposite to the direction indicated by the arrow R in FIG. 15B, the first protruding portion 216 of the jig 200 presses the wall surface 64a of the storage portion 64 of the main body 52 of the distal framing portion 22. The opposed surface 218a of the second protruding portion 218 maintains the contact with the distal side covering portion 126a of the distal side edge 126 of the cover 14. As a result, the distal framing portion 22 and the cover 14 will turn in the same direction as the jig 200. The distal framing portion 22 will therefore be prevented from receiving a load from the jig 200, and the cover 14 will not be removed from the distal framing portion 22.

As described above, the endoscope 10 according to the present embodiment realizes the following.

The disposable type cover 14 can be used for the distal framing portion 22. For such a distal framing portion 22, even the back side of the swing table 42 can be easily washed with a brush or the like.

The fragile portion 156 is formed so that the annular portion 114 can split along an axis parallel to or substantially parallel to the longitudinal axis L. That is, the annular portion 114 can be broken at the fragile portion 156 along the longitudinal axis L, and the cover 14 is thereby split in the circumferential direction at the breakage portion B formed as a crack (breakage surface) along the longitudinal axis L.

After breaking the fragile portion 156, at least part of the breakage portion B becomes visibly recognizable. The coupling portion 156c of the cover main body 102 having a cut length which is short can be spread open wide on the proximal side together with the slits 156a and 156b. In addition, since a space is created immediately below the fragile portion 156, the breaking sound can be reverberated when breaking (cutting) the fragile portion 156. Thus, the user who removes the cover 14 from the distal framing portion 22 can see the breakage of the fragile portion 156 of the cover 14 and hear the breaking sound.

When attaching the cover 14 to the distal framing portion 22, the fragile portion 156 formed by the slits 156a and 156b can be used to facilitate the elastic deformation. Moreover, the guide groove 70 and the guide protruding portion 154 facilitate the positioning of the cover 14 at a predetermined position in the turning direction (peripheral direction).

When removing the cover 14 from the distal framing portion 22, the depressed portion 124 of the open edge 116 is pressed open. At this point, the retention portions of the distal framing portion 22 and the cover 14 (i.e., the guide groove 70 of the distal framing portion 22 and the guide protruding portion 154 of the cover 14) are formed firmly enough to withstand the force in the turning direction of the longitudinal axis L. Thus, the retention portions act to maintain the engagement even under the force applied in the peripheral direction of the cover 14. The stress therefore can be concentrated in the fragile portion 156 of the cover 14, and the force for removal of the cover 14 can be concentrated to break the fragile portion 156 and disengage the lock portions (i.e., the lock pin 74 of the distal framing portion 22 and the lock depressed portion 152 of the cover 14). That is, the force for removal of the cover 14 can be concentrated at the fragile portion 156. Furthermore, the lock depressed portion 152 of the cover 14 can be disengaged from the lock pin 74 of the distal framing portion 22 by the momentum of the stress that is released by the breakage of the coupling portion 156c of the fragile portion 156. As a result, the breakage of the fragile portion 156 and disengagement of the lock portions (the lock pin 74 of the distal framing portion 22 and the lock depressed portion 152 of the cover 14) can be performed at approximately the same time.

Here, the engagement distance of the guide protruding portion 154 of the cover 14 with the guide groove 70 of the distal framing portion 22 is set long. Thus, when breaking the cover 14 by use of the jig 200, the pressing force onto the cover 14 can be further concentrated on the breakage of the fragile portion 156 and the disengagement of the lock portions (the lock pin 74 of the distal framing portion 22 and the lock depressed portion 152 of the cover 14).

The fragile portion 156 and the lock depressed portion 152 are formed at positions approximately 90° apart from each other in the peripheral direction of the longitudinal axis L. Moreover, the distal side covering portion 126a of the cover 14 is on the distal side of the flat portion 62. This regulates the movement of the distal side covering portion 126a with respect to the right side edge 122 in the peripheral direction. Thus, when the pressing force is applied to open the depressed portion 124 of the open edge 116, the distal side edge 126 maintains its position, while the right side edge 122 moves in the peripheral direction to break the fragile portion 156. At the same time, the lock depressed portion 152 can be disengaged from the lock pin 74.

In particular, the fragile portion 156 of the cover 14 is preferably formed at a position away from the guide protruding portion 154 of the cover 14 in the peripheral direction of the central axis C, or in other words, at a position close to the lock depressed portion 152. With such an arrangement, the deformation amount of the fragile portion 156 can be increased in comparison with the deformation amount of the guide protruding portion 154 of the cover 14 in the peripheral direction of the central axis C. As a result, the fragile portion 156 can be reliably broken when removing the cover 14 from the distal framing portion 22.

It should be noted that the cover 14 is often far smaller than the user's hand. When the user is removing the cover 14 using the force of the hand, the movement of the hand with respect to the cover 14 is not regulated. On the other hand, the maximum turn amount with respect to the distal framing portion 22 can be regulated by the support peripheral surface 214 of the jig 200 and the rotation peripheral surface 158 of the cover 14. By using the jig 200, the cover 14 can be removed from the distal framing portion 22 in a series of operations. The user therefore can be prevented from removing the cover 14 by excessive force of the user's hand when the jig 200 is used to remove the cover 14 from the distal framing portion 22.

The cover 14 attached to the distal framing portion 22 is configured so that when the jig 200 is adopted, the user indirectly breaks the fragile portion 156 with the jig 200 applying a stress at a position away from the fragile portion 156 (a position indicated by a reference number 123), instead of directly breaking the fragile portion 156 itself. Moreover, when the jig 200 is used, at least part of the fragile portion 156 is exposed. Therefore, the user can perform the breaking operation while directly visually observing the fragile portion 156.

Furthermore, when the cover 14 is removed from the distal framing portion 22 by use of the jig 200, the distal framing portion 22 will not be brought into contact with any position of the jig 200, from the beginning to the end of the application of stress for the removal. The jig 200 is therefore prevented from applying a load to the distal framing portion 22.

In light of the above, the present embodiment offers the endoscope cover 14 that can be easily removed from the distal framing portion 22 of the insertion section 12, as well as the endoscope 10 having such an endoscope cover 14, the cover unit, and the endoscope unit.

In the present embodiment, the example in which the lock pin 74 includes the inclined plane 74a has been described, but the inclined plane 74a is not necessarily required.

In the embodiment, the example in which the lock pin 74 is arranged in the distal framing portion 22 to protrude outwardly in the radial direction with the lock depressed portion 152 arranged in the inner endoscope cover 14 has been described, but the arrangement of the projection and depression may be reversed. That is, a lock depressed portion may be formed in the distal framing portion 22, and a lock pin may be formed in the endoscope cover 14 to be engaged with the lock depressed portion.

In the present embodiment, the example is described as turning the jig 200 with respect to the distal framing portion 22 around the center axis C if the jig 200 is adopted to remove the cover 14 attached to the distal framing portion 22. Alternatively, when the jig 200 shown in FIGS. 18A and 18B is adopted, the jig 200 is not necessarily turned but may be simply moved along the center axis C with respect to the cover 14 attached to the distal framing portion 22.

Figure 18A:
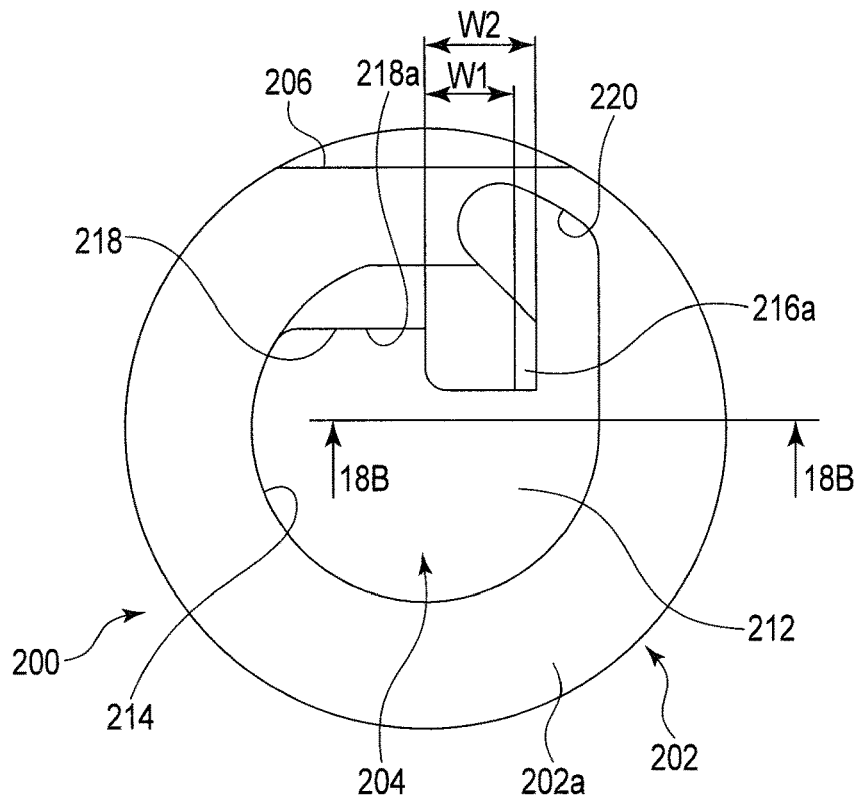
FIG. 18A is a schematic front view showing the acting portion at one end of a jig that is different from that of FIG. 14A, for removing the endoscope cover from the distal framing portion of the endoscope according to the first and second embodiments.
Figure 18B:
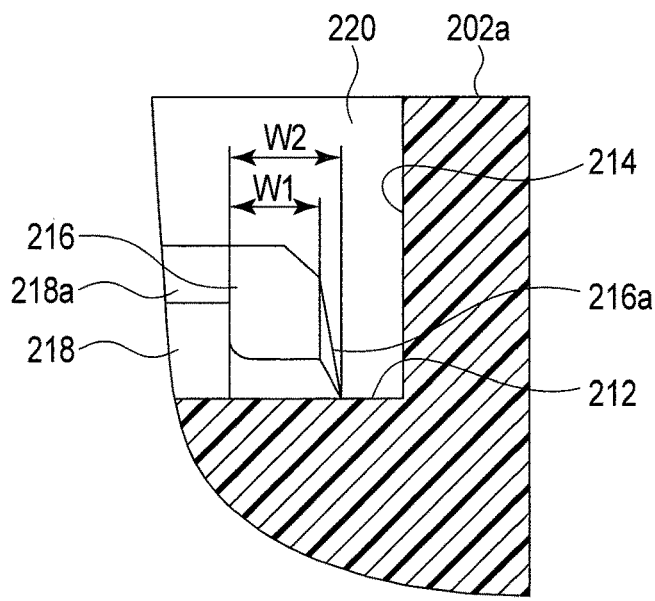
FIG. 18B is a schematic cross-sectional view taken along line 18B-18B in FIG. 18A.

In the jig 200, as shown in FIGS. 18A and 18B, the first protruding portion 216 of the acting portion 204 includes the pressure portion 216a that is formed as an inclined surface. The width of the pressure portion 216a of the first protruding portion 216 increases from W1 to W2 along the first protruding portion 216 from the one end 202a of the column 202 toward the bottom surface 212.

The operation using the jig 200 shown in FIGS. 18A and 18B will be briefly described.

As shown in FIG. 15A, the acting portion 204 of the jig 200 is brought to the position shown in FIG. 15B and fitted onto the distal framing portion 22 with the cover 14 attached. Here, even if the jig 200 is not turned around the axis of the central axis C, the pressure portion 216a that is formed as the inclined surface of the first protruding portion 216 presses the pressure receiving portion 123 in the peripheral direction of the central axis C. With such a structure, when the jig 200 shown in FIG. 18A is moved along the central axis C, stress is applied to the cover 14 attached to the distal framing portion 22 around the central axis C in the same manner as turning the jig 200 of FIG. 11A around the central axis C, and the fragile portion 156 is thereby broken. At the same time as the breakage of the fragile portion 156, the engagement of the lock depressed portion 152 of the cover 14 with the lock pin 74 of the distal framing portion 22 is released.

In this case also, the guide protruding portion 154 of the cover 14 acts to maintain the engagement with the guide groove 70 of the distal framing portion 22, as described above. The guide protruding portion 154 therefore can regulate the movement of the cover main body 102 around the center axis C with respect to the distal framing portion 22.

As described above, even when the jig 200 is fitted onto the cover 14 attached to the distal framing portion 22, the fragile portion 156 is exposed. That is, the jig 200 will not cover the fragile portion 156 and the lock depressed portion 152. The user is therefore allowed to directly observe the state of the fragile portion 156. If the fragile portion 156 is not broken by the inclined pressure portion 216a, the jig 200 may then be turned around the central axis C, as described above.

Modifications of the first embodiment are now briefly described. It should be noted that these modifications can be suitably combined.

In the example shown in FIGS. 19A and 19B, the shape of the fragile portion 156 differs from the fragile portion 156 described in the first embodiment.

As shown in FIG. 19A, the fragile portion 156 includes a first thin portion 256a, a second thin portion 256b, and a coupling portion 256c. It is preferable that, as shown in FIG. 19B, the first thin portion 256a and the second thin portion 256b be formed to be flush in the circumferential direction with the rest of the outer peripheral surface of the cover main body 102 that is adjacent to these thin portions, and that the inner peripheral surface 102a be formed into a depression. The first thin portion 256a functions in the same manner as the slit 156a described in the first embodiment. The second thin portion 256b functions in the same manner as the slit 156b described in the first embodiment.

The slit 156a described in the first embodiment may of course be used in place of the first thin portion 256a, or the slit 156b described in the first embodiment may be used in place of the second thin portion 256b. This also applies to the modification examples described later.

In the example shown in FIG. 19A, the guide protruding portion 154 is not provided. The guide protruding portion 154 does not necessarily need to be formed. This means that the guide groove 70 in the distal framing portion 22 also does not necessarily need to be formed.

When the jig 200 (see FIGS. 13 to 16E) described in the first embodiment is adopted to remove the cover 14 from the distal framing portion 22, the operation force of the jig 200 is applied to the lock depressed portion 152 of the cover 14 through the pressure receiving portion 123 and the right side edge 122 of the cover 14. At this point, the guide groove 70 (see FIGS. 2A and 6) of the distal framing portion 22 and the guide protruding portion 154 of the cover 14 (see FIG. 6) are not provided. However, the distal-most part of the bending portion 24 is gripped by the user, so the distal framing portion 22 is prevented from being turned around the central axis C. Therefore, in the same manner as described in the first embodiment, the distal framing portion 22 is not turned, but only the cover 14 is turned by the use of the jig 200. Thus, the fragile portion 156 can be broken in the same manner as in the first embodiment. At the breakage, a breaking sound is generated from the fragile portion 156. In addition, the user can check the state by visually observing the breakage portion B of the fragile portion 156.

Figure 20A:
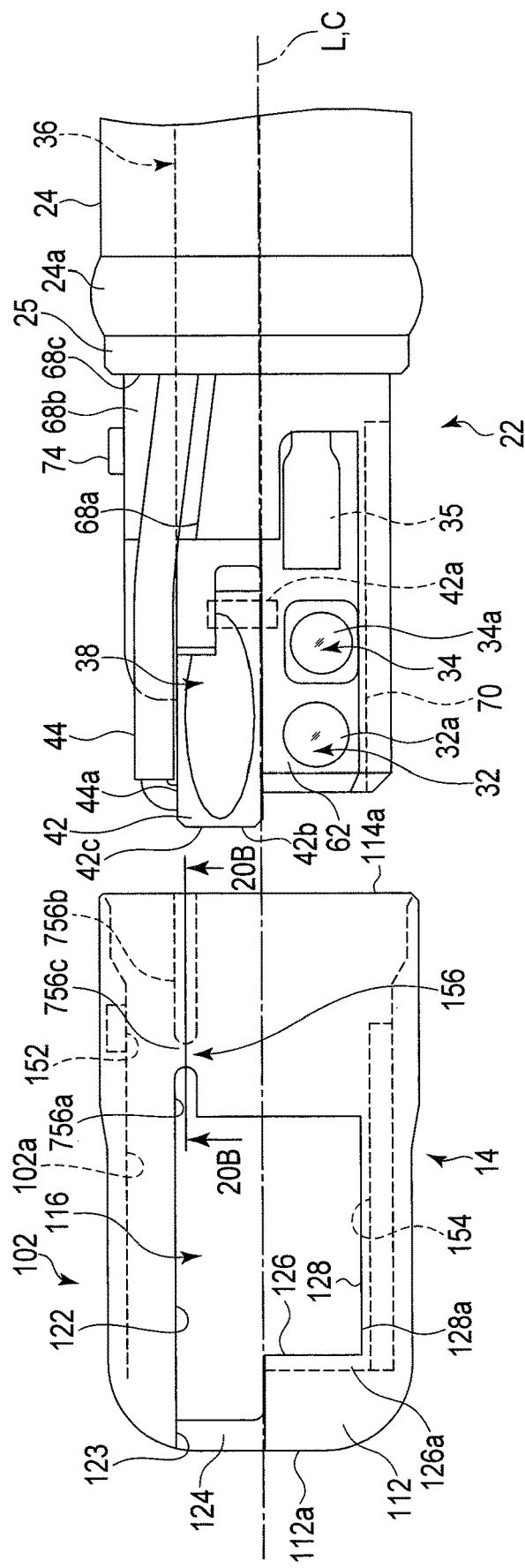
FIG. 20A is a schematic perspective view showing the endoscope cover currently being attached to the distal framing portion of the endoscope according to a modification example (second modification example) of the first embodiment.

In the example shown in FIG. 20A, the cover main body 102 and the presser ring 104 are not separate bodies (see FIG. 4A), but are formed in an integral unit. In this modification example, the presser ring 104 made of a rubber material is not included.

Figure 20B:
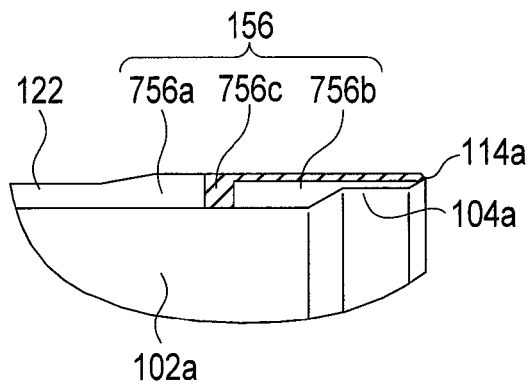
FIG. 20B is a schematic longitudinal sectional view taken along line 20B-20B in FIG. 20A.

As shown in FIGS. 20A and 20B, the fragile portion 156 of the cover main body 102 includes a slit 756a, a thin portion 756b, and a coupling portion 756c. The coupling portion 756c is formed between the slit 756a and the thin portion 756b. It is preferable that the thin portion 756b be continuous with the proximal end 114a of the cover main body 102. Thus, even when the cover main body 102 is formed integrally with the presser ring 104, the cover 14 shown in FIG. 20A can be used in the same manner as the cover 14 described in the first embodiment (see FIG. 5A).

Figure 20C:
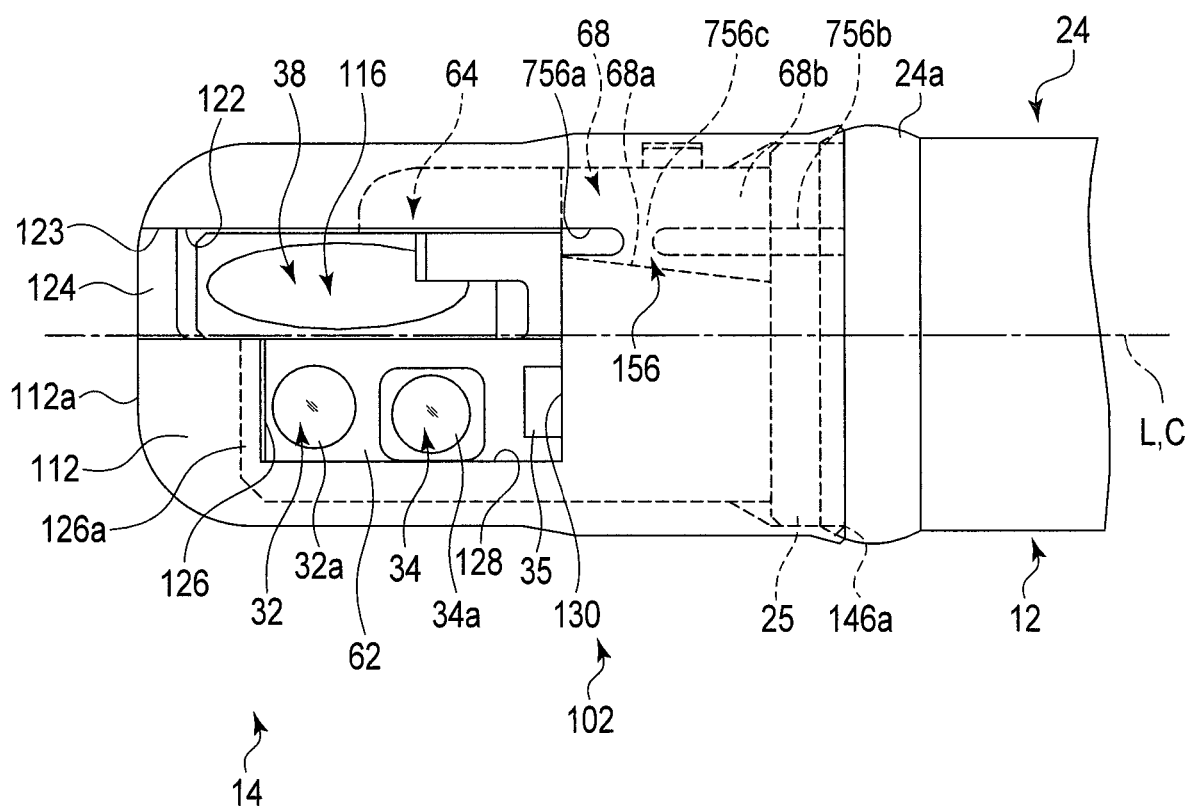
FIG. 20C is a diagram of the endoscope cover attached to the distal framing portion of the endoscope according to the modification example (second modification example) of the first embodiment, as viewed from the arrow 8A side of FIG. 7.

As shown in FIG. 20C, the cover 14 is attached to the distal framing portion 22 in the same manner as in FIG. 8A. The wire moving portion (wire moving region) 68 is provided inside at a position corresponding to where the fragile portion 156 of the cover main body 102 is formed. In particular, the coupling portion 756c of the fragile portion 156 to be broken is provided in the same space as the wire moving portion 68.

Figure 21:
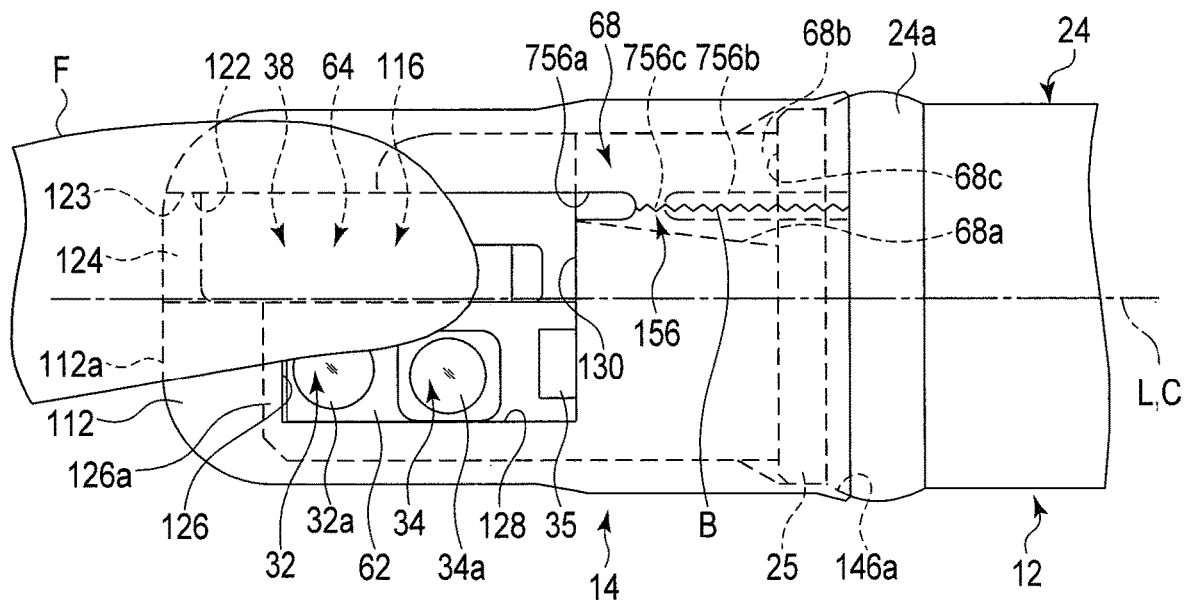
FIG. 21 is a schematic top view showing the endoscope cover attached to the distal framing portion of the endoscope according to the modification of the first embodiment in a state in which the fragile portion has been broken by pressing the pressure receiving portion farther from the fragile portion with a finger.
Figure 22:
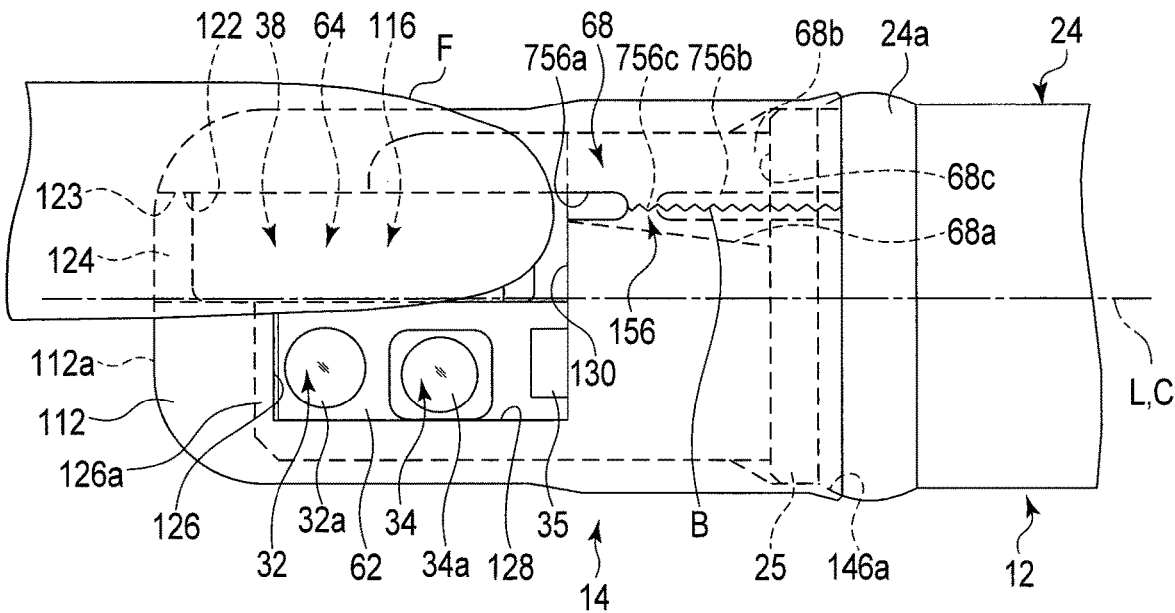
FIG. 22 is a schematic top view showing the endoscope cover attached to the distal framing portion of the endoscope according to the modification example of the first embodiment in a state in which the fragile portion has been broken by pressing the right side edge closer to the fragile portion with a finger.

When the cover 14 is removed from the distal framing portion 22, the coupling portion 756c between the slit 756a and the thin portion 756b may be broken by the force of the user's finger F, as shown in FIGS. 21 and 22, for example. At this time, the fragile portion 156 may be broken from the coupling portion 756c to the proximal end of the thin portion 756b, which coincides with the proximal end 114a of the cover 14. The cover 14 in this example is entirely made of a plastic material, and the presser ring 104 made of a rubber material is not provided to cover the outer periphery of the proximal end portion of the annular portion 114. This prevents the breaking sound that occurs in accordance with the breakage of the breakage portion B from being attenuated at the presser ring 104. In addition, since the presser ring 104 of a rubber material is not provided to cover the outer periphery of the proximal end portion of the annular portion 114, the user can visually check the breakage portion B from its distal end to its proximal end.

In the example shown in FIG. 21, the pressure receiving portion 123 of FIG. 9, for example, is pressed to pull the right side edge 122 away from the wall surface 64a of the storage portion 64, as in FIGS. 10 and 11. On the other hand, the cover 14 is prevented from being turned in the circumferential direction of the longitudinal axis L due to the engagement of the guide groove 70 and the guide protruding portion 154. Accordingly, the coupling portion 756c of the fragile portion 156 is cracked in a direction orthogonal to the direction in which the breaking force is applied (i.e., direction along the longitudinal axis L), and the coupling portion 756c is broken along the longitudinal axis L. At this breakage, the engagement of the lock depressed portion 152 with the lock pin 74 of the distal framing portion 22 is released. With such a configuration, the user can directly observe the breakage portion B of the fragile portion 156.

Along with the breakage of the coupling portion 756c between the slit 756a and the thin portion 756b, a breaking sound is generated. The wire moving portion 68 serves to reverberate the breaking sound of the coupling portion 756c between the walls 68a, 68b, and 68c and the inner peripheral surface 102a of the cover main body 102.

The user therefore can directly visually check and recognize the breakage portion B of the fragile portion 156, and also can recognize the breakage by hearing the breaking sound.

The position to press the cover 14 with the finger F is not limited to the pressure receiving portion 123 indicated in FIG. 21. The position to press the cover 14 with the finger F may be, for example, the portion of the right side edge 122 that is close to the fragile portion 156, as shown in FIG. 22. With this arrangement, the fragile portion 156 can be broken in the same manner as in FIG. 21. Therefore, even when the user places the finger F at the position of the right side edge 122 indicated in FIG. 22 and applies a stress to break the fragile portion 156, the user can directly observe and recognize the breakage portion B of the fragile portion 156 and also recognize the breakage when hearing the breaking sound.

After the cover 14 is turned around the central axis C with respect to the distal framing portion 22 and the engagement of the lock depressed portion 152 is released with the lock pin 74 as the fragile portion 156 is broken, the cover 14 can be moved toward the distal side with respect to the center axis C, and removed from the distal framing portion 22.

Figure 23A:
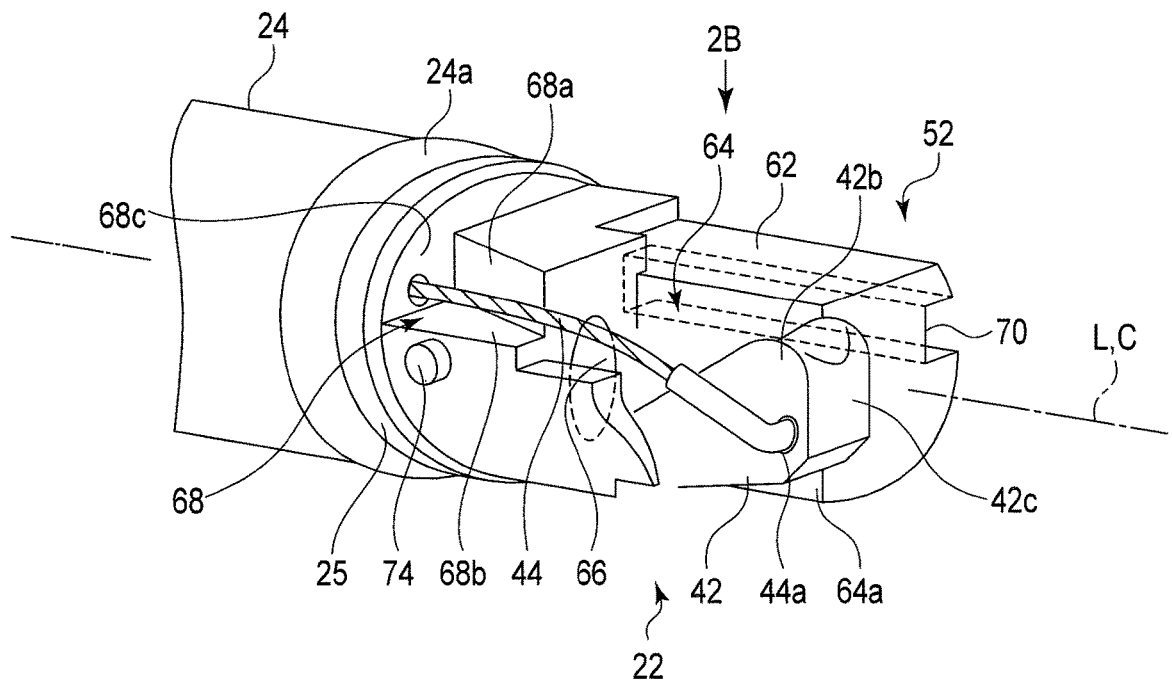
FIG. 23A is a schematic perspective view showing the distal framing portion of the endoscope according to a modification example (another modification example) of the first embodiment.
Figure 23B:
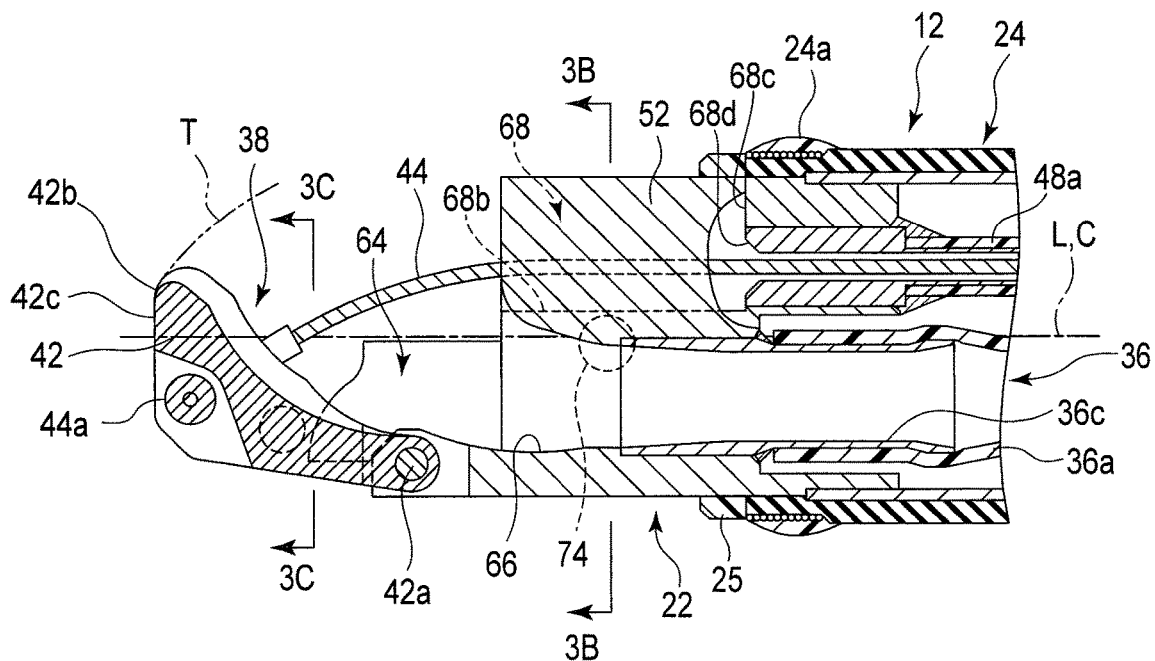
FIG. 23B is a schematic longitudinal sectional view showing the distal framing portion of the endoscope according to a modification example (another modification example) of the first embodiment.

According to the first embodiment, the wire cover 45 is provided on the outer periphery of the wire 44, but the wire cover 45 is not necessarily required, as indicated in FIGS. 23A and 23B. Without the wire cover 45, a known structure using an O-ring (not shown) may be provided, for example, in the vicinity of the operation section 16 to prevent any liquid or gas from entering the inside of the tubular portion 26 of the insertion section 12, or in other words between the bending portion 24/tubular portion 26 and the tube 48a through which the wire 44 passes (see FIG. 1).

Even with such an arrangement, the air propagation sound can be transmitted through the opening 68d to the inside of the tube 48a. The tube 48a is designed to be water-tight by a known mechanism. Thus, the breaking sound can be reverberated in the same manner as in the first embodiment.

Next, the second embodiment will be described with reference to FIGS. 24 to 27. This embodiment is a modification of the first embodiment including its modification examples, and the same reference numerals are given to the same components as described in the first embodiment or components having the same function, and detailed description is omitted.

Figure 24:
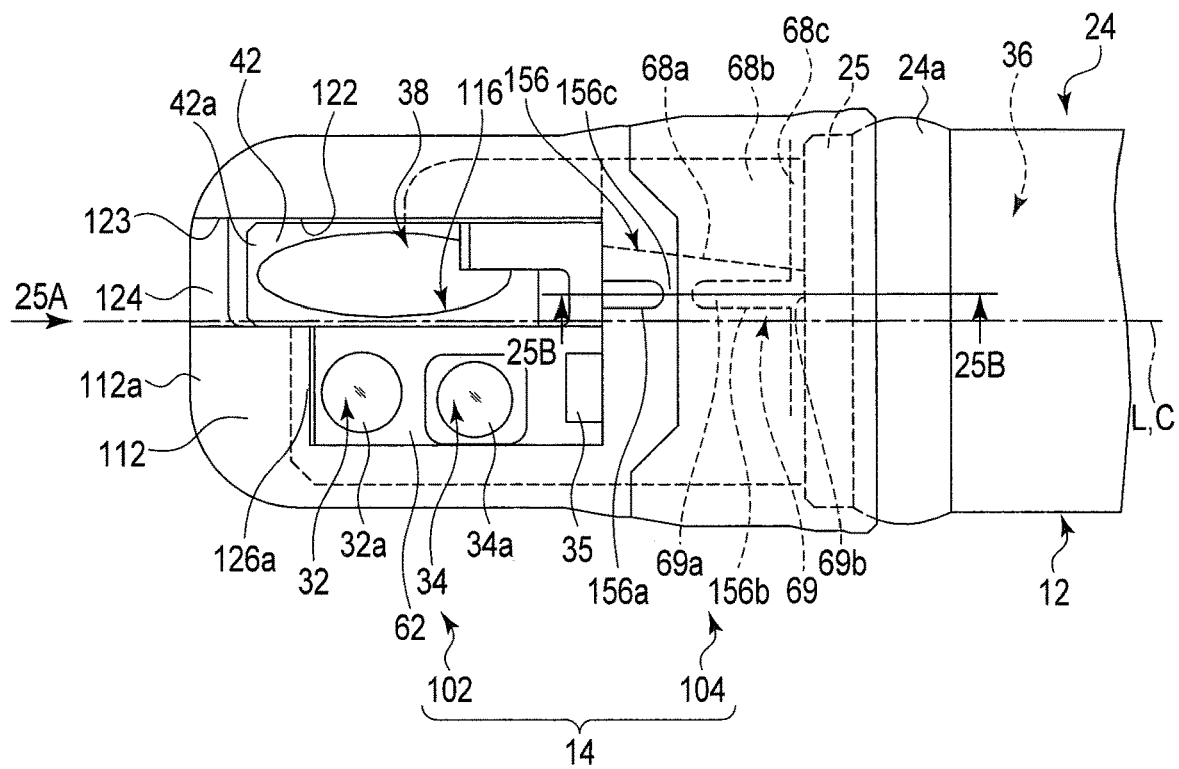
FIG. 24 is a diagram of the endoscope cover attached to the distal framing portion of the endoscope according to the second embodiment, as viewed from the arrow 8A side of FIG. 7.

According to this embodiment, the fragile portion 156 is disposed at a position shifted from the wire moving portion (wire moving region) 68 of the distal framing portion 22 toward the side closer to the flat portion 62, as shown in FIG. 24. In other words, the wire moving portion 68 is not provided under the fragile portion 156. It is preferable, however, that the area (gap) under the fragile portion 156 be continuous with the wire moving portion 68, as will be described later.

Figure 25A:
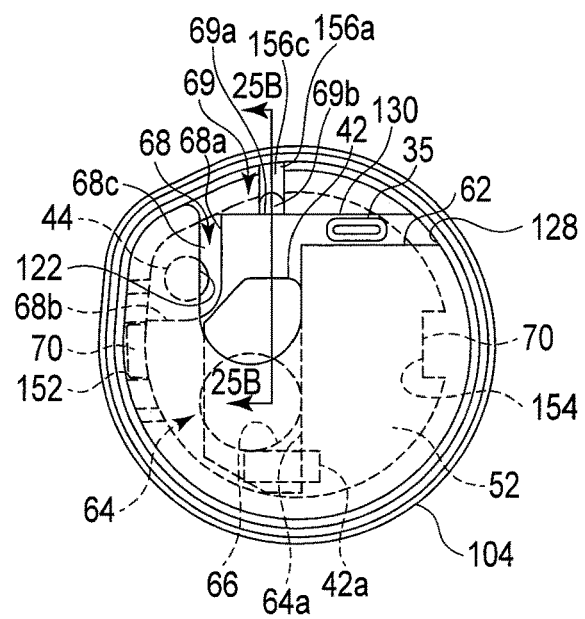
FIG. 25A is a diagram, as viewed from the arrow 25A side of FIG. 24.
Figure 25B:
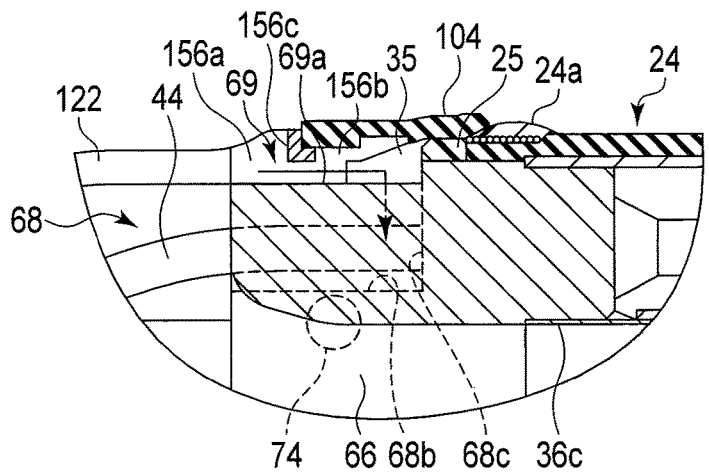
FIG. 25B is a schematic vertical sectional view, taken along line 25B-25B in FIG. 24.

As shown in FIGS. 25A and 25B, the main body 52 includes a wall (bottom surface) 69a that is orthogonal to the wall 68a at a position adjacent to the flat portion 62 with respect to the wire moving portion 68. This wall 69a is preferably parallel to the flat portion 62. A space 69 is formed by the wall 69a, together with a wall (proximal end face) 69b continuous with the wall 68c and the inner peripheral surface 102a of the cover main body 102. It is preferable that the wall 69a be formed as a surface along the longitudinal axis L. The wall 69b is formed as a surface intersecting the longitudinal axis L. The space 69 is spaced apart from at least part of the inner peripheral surface 102a of the cover main body 102, forming a gap (suitable region). The fragile portion 156 is positioned so as to be continuous with at least part of the space (gap) 69, with the cover 14 attached to the distal framing portion 22. The space 69 adjacent to the fragile portion 156 (i.e., the distance from the fragile portion 156 to the wall 69a) is preferably equal to, or larger than, the thickness of the cover main body 102 before the fragile portion 156 is broken. With such a space 69, the fragile portion 156 can be broken by directly pressing with the finger F. In addition, the breaking sound of the fragile portion 156 can be reverberated in the space 69.

With the wall 69b of the space 69 that is continuous with the wall 68c of the wire moving portion 68, the space 69 is in communication with the wire moving portion 68.

Figure 26:
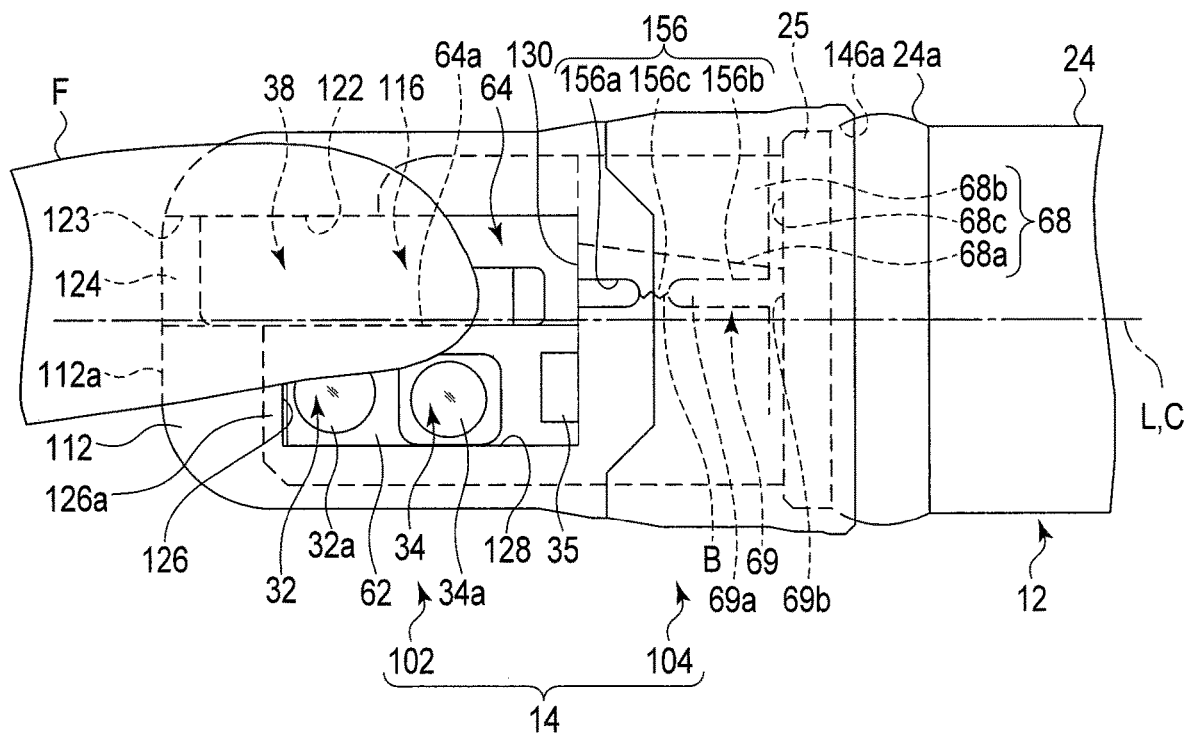
FIG. 26 is a schematic top view showing the endoscope cover attached to the distal framing portion of the endoscope according to the second embodiment in a state in which the fragile portion is broken by pressing with a finger the pressure receiving portion farther from the fragile portion.

When the cover 14 is removed from the distal framing portion 22, the force of the user's finger F is used to break the coupling portion 156c between the slits 156a and 156b, as shown in FIGS. 26 and 27, for example.

In the example shown in FIG. 26, the pressure receiving portion 123 shown in FIG. 9 is pressed to spread the right side edge 122 away from the wall surface 64a of the storage portion 64, in the same manner as in FIGS. 10 and 11. Furthermore, the cover 14 is prevented from being turned in the circumferential direction of the longitudinal axis L due to the engagement of the guide groove 70 and the guide protruding portion 154. As a result, the coupling portion 156c of the fragile portion 156 is cracked in a direction orthogonal to the direction of the application of the breaking force (i.e., along the longitudinal axis L), and is broken along the longitudinal axis L. At this breakage, the engagement of the lock depressed portion 152 with the lock pin 74 of the distal framing portion 22 is released. With such a configuration, the user can directly visually check the breakage portion B of the fragile portion 156.

In accordance with the breakage of the coupling portion 156c between the slits 156a and 156b, a breaking sound is generated. As the breaking sound, a solid propagation sound transmitting through the cover 14 and an air propagation sound transmitting through the air are generated. The space 69 under the fragile portion 156 includes the walls 69a and 69b, and the wire moving portion 68 that communicates with the space 69 includes the walls 68a, 68b, and 68c. With such an arrangement, the air propagation sound of the breaking sound is suitably reflected between the inner peripheral surface 102a of the cover main body 102 and the walls 69a and 69b. Furthermore, since the space 69 communicates with the wire moving portion 68, the air propagation sound of the breaking sound is reflected not only between the inner peripheral surface 102a of the cover main body 102 and the walls 69a and 69b, but also between the peripheral surface 102a of the cover main body 102 and the walls 68a, 68b, and 68c. For this reason, the air propagation sound of the breaking sound is reflected between the inner peripheral surface 102a of the cover main body 102, the space 69, and the wire moving portion 68.

The walls 68a, 68b, 68c, 69a, and 69b are respectively formed of a metal material such as a stainless steel material into a flat surface, with minimal unevenness. Thus, the sound is well reflected and hardly absorbed, in comparison with a rubber material or the like. By combining the space 69 and the wire moving portion 68 to form an acoustic space with the walls 69a and 69b of the space 69 and the walls 68a, 68b, and 68c of the wire moving portion 68, the breaking sound of the coupling portion 156c can be reverberated, together with the inner peripheral surface 102a of the cover main body 102.

The user can directly visually check and recognize the breakage portion B of the fragile portion 156, and can also recognize the breakage by hearing the breaking sound.

The position to press the cover 14 with the user's finger F is not limited to the pressure receiving portion 123 indicated in FIG. 26. For example, the position to press the cover 14 with the finger F may be the portion of the right side edge 122 that is close to the fragile portion 156, as shown in FIG. 27. With this arrangement, the fragile portion 156 can be broken in the same manner as in FIG. 26. Thus, even when the user places the finger F at the position of the right side edge 122 indicated in FIG. 27 and applies stress to break the fragile portion 156, the user can directly observe and recognize the breakage portion B of the fragile portion 156 and also recognize the breakage when hearing the breaking sound.

After the cover 14 is turned around the central axis C with respect to the distal framing portion 22 and the engagement of the lock depressed portion 152 is released with the lock pin 74 as the fragile portion 156 is broken, the cover 14 can be moved toward the distal side with respect to the center axis C, and removed from the distal framing portion 22.

In the first and second embodiments described above, the normal line N (see FIGS. 2C, 3B, and 3C) to the flat portion 62 in which the illumination window 32a and the observation window 34a are provided is indicated in the direction substantially orthogonal to the longitudinal axis L. The direction of the normal line N to the flat portion 62, however, can be suitably determined. If the direction of the normal line N is suitably determined, the shape of the acting portion 204 of the jig 200 can be suitably determined.

According to the first and second embodiments described above, the distal framing portion 22 is of a side-viewing type. Alternatively, the distal framing portion 22 may be formed of a so-called direct-viewing type, with which an observation is conducted in the direction along the longitudinal axis L of the insertion section 12, or of a so-called oblique-viewing type, with which an observation is conducted in a suitable direction between the direction along the longitudinal axis L of the insertion section 12 and the direction orthogonal to the longitudinal axis L.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope cover that is to be attached to a distal framing portion of an insertion section of an endoscope, the endoscope cover comprising:
   a cylindrical cover main body that is to be attached to the distal framing portion along a longitudinal axis of the insertion section, the cover main body including:
      an opening formed on a lateral side surface of the cylindrical cover main body so as to be open in a direction orthogonal to the longitudinal axis,
      an annular portion that is to cover a part of an outer periphery of the distal framing portion, and
      a fragile portion, at least a part of which is provided on the annular portion of the cover main body, the cover main body being spaced apart from at least a part of the distal framing portion and forming a gap between the cover main body and the distal framing portion; and the fragile portion including:
a first slit provided on an edge of the opening of the cover main body, the first slit extending proximally from a proximal end of the opening,
a second slit provided on a proximal end of the annular portion, the second slit extending distally from the proximal end of the annular portion, and
a coupling portion provided between the first slit and the second slit, wherein the coupling portion of the fragile portion is configured to be broken under application of an intended stress from an outside, and the fragile portion being configured to reverberate a breaking sound of the coupling portion in cooperation with the gap when the coupling portion is broken.

2. The endoscope cover according to claim 1, wherein the fragile portion is configured to generate a sound from broken surfaces of the fragile portion in cooperation with the gap when the intended stress is re-applied to the fragile portion after the fragile portion was broken.

3. The endoscope cover according to claim 1, wherein the fragile portion is arranged at a position that is continuous with at least a part of the gap when the endoscope cover is attached to the distal framing portion.

4. The endoscope cover according to claim 1, wherein a distance between an inner peripheral surface of the cover main body and a surface of the distal framing portion that faces the inner peripheral surface of the cover main body to form the gap is equal to, or greater than, a thickness of the cover main body.

5. The endoscope cover according to claim 1, wherein the fragile portion is configured to reverberate the breaking sound when the coupling portion is broken under the intended stress applied to the fragile portion in a circumferential direction of the longitudinal axis of the insertion section, or a radial direction toward the longitudinal axis.

6. A cover unit comprising:
the endoscope cover according to claim 1; and
a jig configured to remove the endoscope cover from the distal framing portion to which the endoscope cover is attached.

7. The cover unit according to claim 6, wherein at least a part of the fragile portion is exposed to an outside when the jig is fitted onto the endoscope cover that is attached to the distal framing portion.

8. The cover unit according to claim 6, wherein:
the jig is configured to rotate around the longitudinal axis when the jig is fitted onto the endoscope cover that is attached to the distal framing portion, and
the coupling portion of the fragile portion is broken under rotation of the jig.

9. The endoscope cover according to claim 1, wherein the first slit, the coupling portion, and the second slit are arranged along the longitudinal axis of the insertion portion of the endoscope when the cover main body is attached to the distal framing portion.

10. An endoscope comprising:
a distal framing portion of an insertion section that is to be inserted into a lumen; and
an endoscope cover attached to the distal framing portion along a longitudinal axis of the insertion section, the endoscope cover comprising:
a cylindrical cover main body that is to be attached to the distal framing portion along a longitudinal axis of the insertion section, the cover main body including:
an opening,
an annular portion that is to cover a part of an outer periphery of the distal framing portion, and
a fragile portion, at least a part of which is provided on the annular portion of the cover main body,
the cover main body being spaced apart from at least a part of the distal framing portion and forming a gap between the cover main body and the distal framing portion; and
the fragile portion including:
a first slit provided on an edge of the opening of the cover main body,
a second slit provided on a proximal end of the annular portion, and
a coupling portion provided between the first slit and the second slit, wherein the coupling portion of the fragile portion is configured to be broken under application of an intended stress from an outside, and the fragile portion being configured to reverberate a breaking sound of the coupling portion in cooperation with the gap when the coupling portion is broken.

11. The endoscope according to claim 10, wherein engagement of a first lock portion provided in the distal framing portion with a second lock portion provided in the cover main body is released when the fragile portion is broken.

12. The endoscope according to claim 11, wherein:
the first lock portion includes a lock pin that is fixed to a pin fixing portion of the distal framing portion, and
the second lock portion includes a depressed portion which is provided on an inner peripheral surface of the annular portion, and which is configured to be engaged with the lock pin.

13. The endoscope according to claim 10, wherein the gap is formed by:
a bottom surface of the distal framing portion, which faces an inner peripheral surface of the cover main body and is spaced apart from the inner peripheral surface of the cover main body, and
a proximal surface of the distal framing portion, which is provided at a proximal side of the longitudinal axis with respect to the bottom surface and which intersects with the longitudinal axis, and
a distance between the bottom surface of the distal framing portion and the inner peripheral surface of the cover main body is greater than a thickness of the cover main body.

14. The endoscope according to claim 13, wherein:
the distal framing portion includes, at a distal end of the insertion section,
a swing table of a swing mechanism that is configured to swing a treatment instrument, and
a part of a wire that moves the swing table, and
a space formed between the inner peripheral surface of the cover main body and the swing table is continuous with the gap.

15. The endoscope according to claim 14, wherein the part of the wire is arranged in the gap in a movable manner.

* * * * *